(12) United States Patent
Watkins et al.

(10) Patent No.: US 7,175,996 B1
(45) Date of Patent: *Feb. 13, 2007

(54) METHODS OF OPTIMIZING ANTIBODY VARIABLE REGION BINDING AFFINITY

(75) Inventors: Jeffry D. Watkins, Encinitas, CA (US); William D. Huse, Del Mar, CA (US); Herren Wu, Germantown, MD (US)

(73) Assignee: Applied Molecular Evolution, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/110,141

(22) PCT Filed: Oct. 13, 2000

(86) PCT No.: PCT/US00/28435

§ 371 (c)(1),
(2), (4) Date: Oct. 29, 2002

(87) PCT Pub. No.: WO01/27160

PCT Pub. Date: Apr. 19, 2001

Related U.S. Application Data

(63) Continuation-in-part of application No. 09/434,870, filed on Nov. 4, 1999, now Pat. No. 6,849,925.

(60) Provisional application No. 60/159,689, filed on Oct. 14, 1999.

(51) Int. Cl.
| C12P 21/06 | (2006.01) |
|---|---|
| C12P 21/08 | (2006.01) |
| C07H 21/04 | (2006.01) |
| A61K 39/395 | (2006.01) |

(52) U.S. Cl. .................. 435/69.1; 424/133.1; 435/69.6; 530/387.3; 536/23.53

(58) Field of Classification Search ............ 424/181.1, 424/183.1, 179.1, 143.1, 141.1, 135.1, 134.1, 424/133.1, 130.1; 530/387.1, 387.3, 388.2, 530/388.22, 388.1; 435/7.1, 69.6, 70.1, 328, 435/334, 235.1, 320.1, 326, 456, 69.1, 23.53, 435/6, 69.7; 536/23.53

See application file for complete search history.

(56) References Cited

U.S. PATENT DOCUMENTS

| 5,223,409 A | 6/1993 | Ladner et al. |
|---|---|---|
| 5,225,539 A | 7/1993 | Winter |
| 5,264,563 A | 11/1993 | Huse |
| 5,403,484 A | 4/1995 | Ladner et al. |
| 5,523,388 A | 6/1996 | Huse |
| 5,585,089 A | 12/1996 | Queen et al. |
| 5,589,573 A | 12/1996 | Hagiwara et al. |
| 5,693,762 A | 12/1997 | Queen et al. |
| 5,723,323 A | 3/1998 | Kauffman et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,871,974 A | 2/1999 | Huse |
| 5,976,862 A | 11/1999 | Kauffman et al. |
| 5,977,322 A | 11/1999 | Marks et al. |
| 6,096,551 A | 8/2000 | Barbas et al. |
| 6,312,693 B1 * | 11/2001 | Aruffo et al. |

FOREIGN PATENT DOCUMENTS

| CA | 2125240 A1 | 12/1995 |
|---|---|---|
| CA | 2152240 * | 12/1995 |
| EP | 0 451 216 B1 | 10/1991 |
| EP | 0 519 596 A1 | 5/1992 |
| EP | 0 682 040 B1 | 11/1995 |
| EP | 0 939 127 A2 | 9/1999 |
| WO | WO 99/42075 | 8/1999 |

OTHER PUBLICATIONS

Glaser et al. Journal of Immunology, 1992, 149 (12):3903-3913.*
Huse et al. Inter. Rev. Immunol., 1993, 10:129-137.*
Yelton et al. Journal of Immunology, 1995, 155:1994-2004.*
Rebar et al. Science. 1994. 263; 671-673.*
Söderlind et al. Gene. 160:269-272, 1995.*
Paul W. E., Fundamental Immunology, 3$^{rd}$ ed 1993, pp. 292-295.*
Barbas et al. Proc. Natl. Acad. Sci. USA, 89:4457-4461, 1992.*
Yang et al. Journal of Molecular biology 254:392-403, 1995.*
Wu et al. Journal of Molecular Biology, 294:151-162, 1999.*
Amit et al., "Three-Dimensional Structure of an Antigen-Antibody Complex at 2.8 A Resolution," *Science* 233:747-753 (1986).

(Continued)

*Primary Examiner*—Larry R. Helms
*Assistant Examiner*—David J. Blanchard
(74) *Attorney, Agent, or Firm*—Alejandro Martinez; Mark J. Stewart

(57) ABSTRACT

The present invention relates to compositions and methods of producing higher affinity molecules, and in particular, higher affinity antibodies. Specifically, the invention contemplates methods of mutagenesis to create a population of oligonucleotides coding for altered polypeptides that are expressed in a host cell and subsequently sequenced to determine the amino acid determinants conferring higher affinity.

6 Claims, 2 Drawing Sheets

OTHER PUBLICATIONS

Baca et al., "Antibody humanization using monovalent phage display," *J. Biol Chem* 272:10678-84 (1997).

Baca et al., "Phage display of a catalytic antibody to optimize affinity for transition-state analog binding," *Proc Natl Acad Sci USA* 94:10063-10068 (1997).

Chothia et. al., "Conformations of immunoglobulin hypervariable regions," *Nature* 342:877-883 (1989).

Chothia et al., "Canonical structures for the hypervariable regions of immunoglobulins," *J. Mol. Biol.* 196:901-917 (1987).

Durie et. al., "Antibody to the Ligand of CD40, gp39, Blocks the Occurrence of the Acute and Chronic Forms of Graft-vs-Host Disease," *J Clin Invest* 94:1333-1338 (1994).

Foote and Winter, "Antibody framework residues affecting the conformation of the hypervariable loops," *J Mol Biol* 224:487-499 (1992).

Foy et al., "Immune Regulation by CD40 and its Ligand GP39," *Annu Rev Immunol* 14:591-617 (1996).

Francisco et al., "In Vivo Efficacy and Toxicity of a single-Chain Immunotoxin Targeted to CD40," *Blood* 89:4493-4500 (1997).

Francisco et al., "Activity of a single-Chain Immunotoxin that Selectively Kills Lymphoma and other B-Lineage Cells expressing the CD40 Antigen," *Cancer Res* 55:3099-3104 (1995).

Glaser et al., "Antibody engineering by codon-based mutagenesis in a filamentous phage vector system," *J. Immunology* 149:3903-3913 (1992).

Harris & Bajorath, "Profiles for the analysis of immunoglobulin sequences: Comparison of V gene subgroups," *Prot Sci* 4:306-310 (1995).

Herren et al., "Humanization of a murine monoclonal antibody by simultaneous optimization of framework and CDR residues," J Molecular Biology 294:151-162 (1999).

Huston et al., "Antigen Recognition and Targeted Delivery by the Single-Chain Fv," *Cell Biophysics*, 22:189-224 (1993).

Irving et al., "Affinity maturation of recombinant antibodies using *E. coli* mutator cells," Immunotechnology 2:127-143 (1996).

Jones et al., "Replacing the complementarity-determining regions in a human antibody with those from a mouse," *Nature* 321:522-525.

Jönsson and Malmquist, "Real Time Biospecific Interaction Analysis," *Advances in Biosnsors*, 2:291-336 (1992).

Kabat et al., *Sequences of protein of immunological interest.*, (5th Ed) Washington DC: United States Department of Health and Human Services (1991).

Kabat et al., "Unusual distributions of amino acids in compementarity determining (hypervariable) segments of heavy and light chains of immunoglobulins and their possible roles in specificity of antibody combining sites," *J. Biol. Chem.* 252, 6609-6616 (1977).

Kristensson et. al., "Humanization of a murine antibody against cryptococcus neoformans polysaccharide using a novel approach," *Vaccines 95*, pp. 39-43 Cold Springs Harbor Laboratory Press, Cold Spring Harbor, NY (1995).

Kunkel, "Rapid and Efficient site-specific mutagenesis without phenotypic selection," *Proc Natl. Acad Sci USA* 82:488-492 (1985).

MacCallum et al., "Antibody-antigen interactions: contact analysis and binding site topgraphy," *J. Mol. Biol.* 262:732-745 (1996).

Mach et al., "Reduction of atherosclerosis in mice by inhibition of CD40 signalling," *Nature* 394:200-203 (1998).

Padlan, "A possible procedure for reducing the immunogenicity of antibody variable domains while preserving their ligand-binding properties," *Mol Immunol* 28:489-498 (1991).

Padlan, "Anatomy of the antibody molecule," *Mol Immunol* 31:169-217 (1994).

Plückthun and Skerra, "Expression of Functional Antibody Fv and Fab Fragments in *Escherichia coli*," *Meth. Enzymol.*, 178:497-515 (1989).

Rader et al., "A phage display approach for repid antibody humanization: Designed combinatorial V gene libraries," *Proc Natl Acad Sci USA* 95:8910-8915 (1998).

Riechmann et al., "Reshaping human antibodies for therapy," *Nature* 332:323-327 (1988).

Rosok et al., "A combinatorial library strategy for the rapid humanization of anticarcinoma BR96 Fab," *J Biol Chem* 271:22611-22618.

Rudikoff et al., "Single amino acid substitution altering antigen-binding specificity," *Proc Natl Acad Sci USA* 79:1979-1983 (1982).

Schier et al., "Isolation of picomolar affinity anti-c-erbB-2 single-chain Fv by molecular evolution of the complementarity determining regions in the center of the antibody binding site," *J Mol Biol* 263:551-567 (1996).

Schreiber & Fersht, "Energetics of protein-protein interactions: Analysis of the barnase-barstar interface by single mutations and double mutant cycles," *J Mol Biol* 248:478-486 (1995).

Singer et al., "Optimal humanization of 1B4, an anti-CD 18 murine monoclonal antibody, is achieved by correct choice of human V-region framework sequences," *J Immunol* 150:2844-2857 (1993).

Stamenkovic et al., "A B-lymphocyte activation molecule related to the nerve growth factor receptor and induced by cytokines in carcinomas," *EMBO J* 8(5): 1403-1410 (1989).

Studnicka et al., "Human-engineered monoclonal antibodies retain full specific binding activity by preserving non-CDR complementarity modulating residues," *Protein Eng* 7:805-814 (1994).

Thompson et al., "Affinity maturation of a high-affinity human monoclonal antibody against the third hypervariable loop of human immunodeficiency virus: Use of phage display to improve affinity and broaden strain reactivity," *J Mol Biol* 256:77-88 (1996).

Uckun et al., "Temporal Association of CD40 Antigen Expression with Discrete Stages of Human B-Cell Ontogeny and the Efficacy of Anti-CD40 Immunotoxins Against Clonogenic B-Lineage Acute Lymphoblastic Leukemia as Well as B-Lineage Non-Hodgkin's Lymphoma Cells," *Blood* 76(12):2449-2456 (1990).

Watkins et al., "Discovery of human antibodies to cell surface antigens by capture lift screening of phage-expressed antibody libraries," *Anal Biochem* 256:169-177 (1998).

Watkins et. al., "Determination of the relative affinities of antibody fragments expressed in *Escherichia coli* by enzyme-linked immunosorbent assay," *Anal Biochem* 253:37-45 (1997).

Wu et al., "Stepwise in vitro affinity maturation of Vitaxin, and $α_vβ_3$-specific humanized mAb," *Proc. Natl. Acad. Sci. USA*, 95:6037-6042 (1998).

Yelton et al., "Affinity maturation of the BR96 anti-carcinoma antibody by codon-based mutagenesis," *J Immunol* 155:1994-2004 (1995).

Queen, C. et al. "A Humanized Antibody That Binds to the Interleukin 2 Receptor." Proc. Natl. Acad. Sci. USA, vol. 86, pp. 10029-10033, 1989.

Co, Man Sung, et al. "Humanized Antibodies For Antiviral Therapy." Proc. Natl. Acad. Sci. USA, vol. 88, pp. 2869-2873, 1991.

* cited by examiner

Vκ Domain

```
        1         10        20        30        40
CD40    DIVLTQSPATLSVTPGDRVSLSCRASQSISDYLHWYQQKSHESPRLLIK
        |        |||| ||||                   ||||      |
VKIII   EIVLTQSPATLSLSPGERATLSCRASQSVSSYLAWYQQKPGQAPRLLIY
                                                       *

50        60        70        80        90        100
CD40    YASHSISGIPSRFSGSGSGSDFTLSINSVEPEDVGIYYCQHGHSFPRTFGGGTKLEIK
                |    |     |   |  ||      |||                  |
VKIII/JK4 DASNRATGIPARFSGSGSGTDFTLTISSLEPEDFAVYYCQQRSNWPLTFGGGTKVEIK
```

VH Domain

```
        1         10        20        30        40
CD40    QIQLVQSGPELKKPGETVRISCKASGYAFTTTGMQWVQEMPGKGLKWIG
        |        |  ||  ||       |       ||| |    |  |
VH7     QVQLVQSGSELKKPGASVKVSCKASGYTFTSYAMNWVRQAPGQGLEWMG
        *                       *       *  **    *   *

50        60        70        80 abc    90
CD40    WINTHSGVPKYVEDFKGRFAFSLETSANTAYLQISNLKNEDTATYFCVR
VH7     WINTNTGNPTYAQGFTGRFVFSLDTSVSTAYLQISSLKAEDTAVYYCAR
                                                       * abcde        110
CD40    SGNGNYDLAYFAYWGQGTLVTVSA
                             |
JH4            YFDYWGQGTLVTVSS
```

Fig. 1

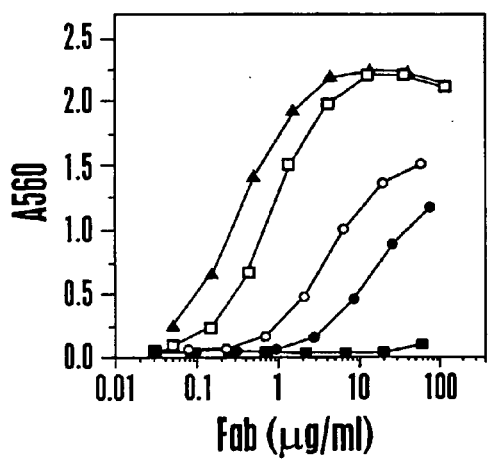

Fig. 2A

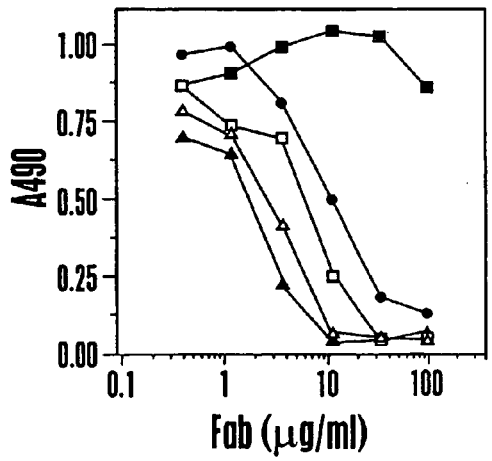

Fig. 2B

METHODS OF OPTIMIZING ANTIBODY VARIABLE REGION BINDING AFFINITY

This application claims benefit under Title 35, United States Code § 119 to PCT/US00/28435 filed on Oct. 13, 2000, which is a continuation-in-part claiming benefit under Title 35, United States Code § 120 to U.S. application Ser. No.: 09/434,870 filed on Nov. 4, 1999, which is now U.S. Pat. No. 6,849,925, which claims benefit to U.S. Provisional Application No. 60/159,689 filed on Oct. 14, 1999.

BACKGROUND OF THE INVENTION

This invention relates generally to a method of monoclonal antibody production and specifically to the simultaneous in vitro affinity optimization of multiple distinct domains of a variable region of a monoclonal antibody.

The War on Cancer is entering its third decade and recent years have shown tremendous progress in the understanding of cancer development and progression yet there has been only marginal decreases in death rates from most types of cancer. Standard chemotherapy and radiation therapy generally involve treatment with therapeutic agents that impact not only cancer cells but other highly proliferative cells of the body, often leading to debilitating side effects. Thus, it is desirable to identify therapeutic agents with a higher degree of specificity for the carcinogenic lesion.

The discovery of monoclonal antibodies (mabs) in the 1970's provided great hope for the reality of creating therapeutic molecules with high specificity. Antibodies that bind to tumor antigens would provide specific targeting agents for cancer therapy. However, while the development of monoclonal antibodies has provided a valuable diagnostic reagent, certain limitations restrict their use as therapeutic entities.

A limitation encountered when attempts are made to use mAbs as therapeutic agents is that since mAbs are developed in non-human species, usually mouse, they elicit an immune response in human patients. Chimeric antibodies join the variable region of the non-human species, which confers binding activity, to a human constant region. However, the chimeric antibody is often still immunogenic and it is therefore necessary to further modify the variable region.

One modification is the grafting of complementarity-determining regions, (CDRs) which are in part antigen binding onto a human antibody variable framework. However, this approach is imperfect because CDR grafting often diminishes the binding activity of the resulting humanized mAb. Attempts to regain binding activity require laborious, step-wise procedures which have been pursued essentially by a trial and error type of approach. For example, one difficulty in regaining binding affinity is because it is difficult to predict which framework residues serve a critical role in maintaining antigen binding affinity and specificity. Consequently, while antibody humanization methods that rely on structural and homology data are used, the complexity that arises from the large number of framework residues potentially involved in binding activity has prevented success.

Combinatorial methods have been applied to restore binding affinity, however, these methods require sequential rounds of mutagenesis and affinity selection that can both be laborious and unpredictable.

Thus, there exists a need for efficient and reliable methods for producing human monoclonal antibodies which exhibit comparable or enhanced binding affinities to their non-human counterparts. The present invention satisfies this need and provides related advantages as well.

SUMMARY OF THE INVENTION

The invention provides a method of conferring donor CDR binding affinity onto an antibody acceptor variable region framework. The method consists of: (a) constructing a population of altered antibody variable region encoding nucleic acids, said population comprising encoding nucleic acids for an acceptor variable region framework containing a plurality of different amino acids at one or more acceptor framework region amino acid positions and donor CDRs containing a plurality of different amino acids at one or more donor CDR amino acid positions; (b) expressing said population of altered variable region encoding nucleic acids, and (c) identifying one or more altered variable regions having binding affinity substantially the same or greater than the donor CDR variable region. The acceptor variable region framework can be a heavy or light chain variable region framework and the populations of heavy and light chain altered variable regions can be expressed alone to identify heavy or light chains having binding affinity substantially the same or greater than the donor CDR variable region. The populations of heavy and light chains additionally can be coexpressed to identify heteromeric altered variable region binding fragments. The invention also provides a method of simultaneously grafting and optimizing the binding affinity of a variable region binding fragment. The method consists of: (a) constructing a population of altered heavy chain variable region encoding nucleic acids comprising an acceptor variable region framework containing donor CDRs and a plurality of different amino acids at one or more framework region and CDR amino acid positions; (b) constructing a population of altered light chain variable region encoding nucleic acids comprising an acceptor variable region framework containing donor CDRs and a plurality of different amino acids at one or more framework regions and CDR amino acid positions; (c) coexpressing said populations of heavy and light chain variable region encoding nucleic acids to produce diverse combinations of heteromeric variable region binding fragments, and (d) identifying one or more heteromeric variable region binding fragments having affinity substantially the same or greater than the donor CDR heteromeric variable region binding fragment. A method of optimizing the binding affinity of an antibody variable region is also provided. The method consists of: (a) constructing a population of antibody variable region encoding nucleic acids, said population comprising two or more CDRs containing a plurality of different amino acids at one or more CDR amino acid positions; (b) expressing said population of variable region encoding nucleic acids, and (c) identifying one or more variable regions having binding affinity substantially the same or greater than the donor CDR variable region. The variable region populations can be heavy or light chains and can be expressed as individual populations or they can be coexpressed to produce heteromeric variable region binding fragments.

BRIEF DESCRIPTION OF THE DRAWINGS

FIG. 1 shows the alignment of anti-CD40 variable region and human template amino acid sequences.

FIG. 2 shows binding reactivity of humanized anti-CD40 variants.

DETAILED DESCRIPTION OF THE INVENTION

Figure 3:
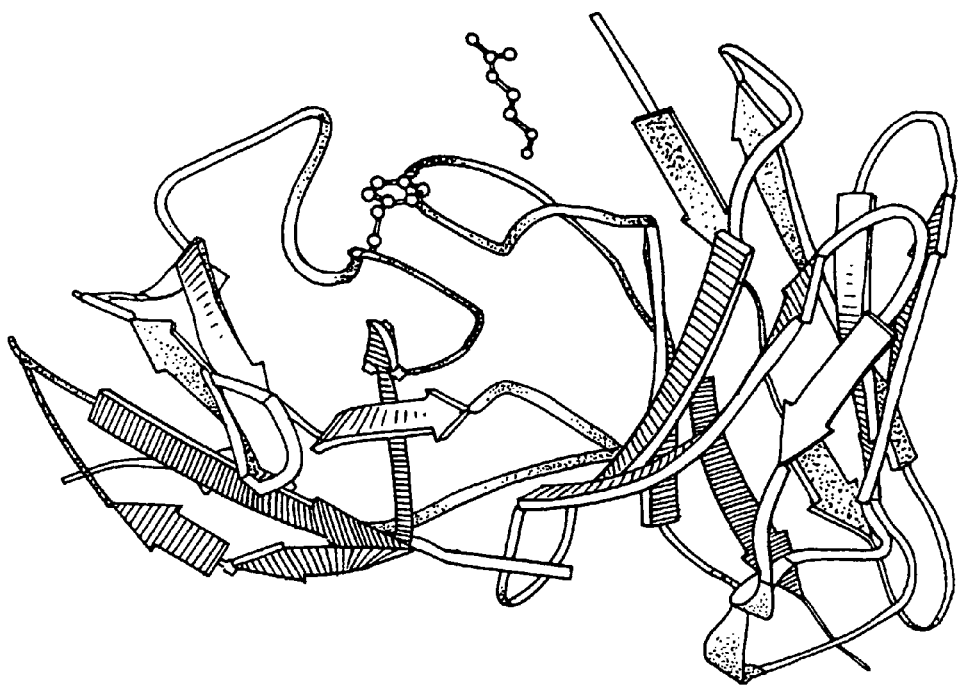
FIG. 3 shows molecular modeling of anti-CD40 variant CW43.
Figure 4A:
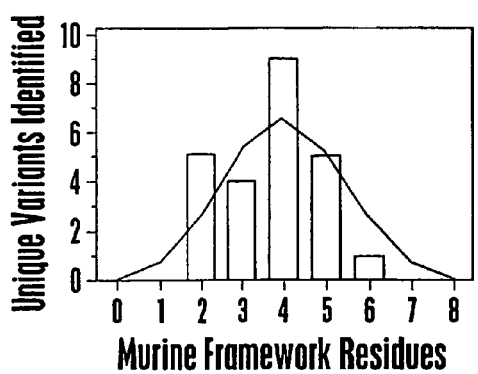
FIG. 4 shows a comparison of the quantitation of murine framework residues in active variants from two libraries.
Figure 4B:
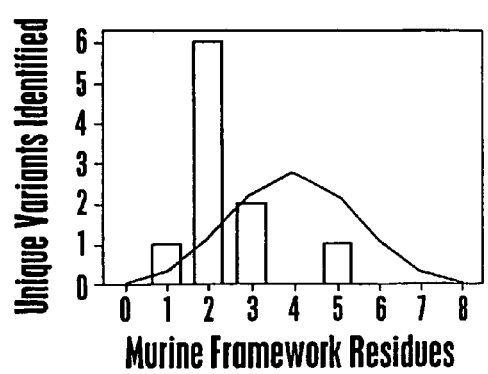

The invention is directed to a method of conferring donor CDR binding affinity onto an antibody acceptor variable region framework. The method effectively combines CDR grafting procedures and affinity reacquisition of the grafted variable region into a single step. The methods of the invention also are applicable for affinity maturation of an antibody variable region. The affinity maturation process can be substituted for, or combined with the affinity reacquisition function when being performed during a CDR grafting procedure. Alternatively, the affinity maturation procedure can be performed independently from CDR grafting procedures to optimize the binding affinity of variable region, or an antibody. An advantage of combining grafting and affinity reacquisition procedures, or affinity maturation, is the avoidance of time consuming, step-wise procedures to generate a grafted variable region, or antibody, which retains sufficient binding affinity for therapeutic utility. Therefore, therapeutic antibodies can be generated rapidly and efficiently using the methods of the invention. Such advantages beneficially increase the availability and choice of useful therapeutics for human diseases as well as decrease the cost to the developer and ultimately to the consumer.

In one embodiment, the invention is directed to methods of producing grafted heavy and light chain variable regions having similar or better binding affinity as the CDR donor variable region. When coexpressed, the grafted heavy and light chain variable regions assemble into variable region binding fragments having similar or better binding affinity as the donor antibody or variable region binding fragments thereof. The grafting is accomplished by generating a diverse library of CDR grafted variable region fragments and then screening the library for binding activity similar or better than the binding activity of the donor. A diverse library is generated by selecting acceptor framework positions that differ at the corresponding position compared to the donor framework and making a library population containing of all possible amino acid residue changes at each of those positions together with all possible amino acid residue changes at each position within the CDRs of the variable region. The grafting is accomplished by splicing a population of encoding nucleic acids for the donor CDR containing species representing all possible amino acid residues at each CDR position into a population of encoding nucleic acids for an antibody acceptor variable region framework which contains species representing all possible amino acid residue changes at the selected framework positions. The resultant population encodes the authentic donor and acceptor framework amino acid sequences as well as all possible combinations and permutations of these sequences with each of the 20 naturally occurring amino acids at the changed positions.

In another embodiment, the invention is directed to methods of producing grafted heavy and light chain variable regions, and heteromeric binding fragments thereof, having similar or better binding affinity as the CDR donor variable region. As described above, the grafting is accomplished by generating a diverse library of CDR grafted variable region fragments and then screening the library for binding activity similar or better than the binding activity of the donor. However, the diverse library is generated by selecting acceptor framework positions that are predicted to affect CDR binding affinity and making a library population containing of all possible amino acid residue changes at each of those positions or subsets of the selected amino acid positions together with all possible amino acid residue changes at each position within the CDRs of the variable region, or subsets of CDR positions. The grafting is accomplished by splicing a population of encoding nucleic acids for the donor CDR containing the selected position changes into a population of encoding nucleic acids for an antibody acceptor variable region framework which contains the selected position changes.

In yet another embodiment, the invention is directed to the optimization of binding affinity of an antibody variable region. The optimization is accomplished by generating a library of variable regions which contain all possible amino acid residue changes at each amino acid position within two or more CDRs. When expressed and screened for binding activity, the variable region, or heavy and light chain heteromeric binding fragments, those species within the population are selected that contain increased or decreased binding activity compared to the parent molecule as optimal binders. Libraries containing subsets, representing less than all amino acid positions within the CDRs, can similarly be generated and screened for selecting optimal binding variable regions and heteromeric binding fragments thereof.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252, 6609–6616 (1977) and Kabat et al., Sequences of protein of immunological interest. (1991), and by Chothia et al., J. Mol. Biol. 196:901–917 (1987) and by MacCallum et al., J. Mol. Biol. 262:732–745 (1996) where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

|  | Kabat[1] | Chothia[2] | MacCallum[3] |
|---|---|---|---|
| $V_H$ CDR1 | 31–35 | 26–32 | 30–35 |
| $V_H$ CDR2 | 50–65 | 53–55 | 47–58 |
| $V_H$ CDR3 | 95–102 | 96–101 | 93–101 |
| $V_L$ CDR1 | 24–34 | 26–32 | 30–36 |
| $V_L$ CDR2 | 50–56 | 50–52 | 46–55 |
| $V_L$ CDR3 | 89–97 | 91–96 | 89–96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is entered to mean all amino acid residues outside the CDR regions within the variable region of an antibody. Therefore, a variable region framework is between about 100–120 amino acids in length but is intended to reference only those amino acids outside of the CDRs.

As used herein, the term "framework region" is intended to mean each domain of the framework that is separated by the CDRs. Therefore, for the specific example of a heavy chain variable region and for the CDRs as defined by Kabat et al., framework region 1 corresponds to the domain of the variable region encompassing amino acids 1–30; region 2 corresponds to the domain of the variable region encompassing amino acids 36–49; region 3 corresponds to the domain of the variable region encompassing amino acids 66–94, and region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above.

As used herein, the term "donor" is intended to mean a parent antibody molecule or fragment thereof from which a portion is derived from, given or contributes to another antibody molecule or fragment thereof so as to confer either a structural or functional characteristic of the parent molecule onto the receiving molecule. For the specific example of CDR grafting, the parent molecule from which the grafted CDRs are derived is a donor molecule. The donor CDRs confer binding affinity of the parent molecule onto the receiving molecule. It should be understood that a donor molecule does not have to be from a different species as the receiving molecule of fragment thereof. Instead, it is sufficient that the donor is a separate and distinct molecule.

As used herein, the term "acceptor" is intended to mean an antibody molecule or fragment thereof which is to receive the donated portion from the parent or donor antibody molecule or fragment thereof. An acceptor antibody molecule or fragment thereof is therefore imparted with the structural or functional characteristic of the donated portion of the parent molecule. For the specific example of CDR grafting, the receiving molecule for which the CDRs are grafted is an acceptor molecule. The acceptor antibody molecule or fragment is imparted with the binding affinity of the donor CDRs or parent molecule. As with a donor molecule, it is understood that an acceptor molecule does not have to be from a different species as the donor.

A "variable region" when used in reference to an antibody or a heavy or light chain thereof is intended to mean the amino terminal portion of an antibody which confers antigen binding onto the molecule and which is not the constant region. The term is intended to include functional fragments thereof which maintain some of all of the binding function of the whole variable region. Therefore, the term "heteromeric variable region binding fragments" is intended to mean at least one heavy chain variable region and at least one light chain variable regions or functional fragments thereof assembled into a heteromeric complex. Heteromeric variable region binding fragments include, for example, functional fragments such as Fab, F(ab)$_2$, Fv, single chain Fv (scFv) and the like. Such functional fragments are well known to those skilled in the art. Accordingly, the use of these terms in describing functional fragments of a heteromeric variable region is intended to correspond to the definitions well known to those skilled in the art. Such terms are described in, for example, Harlow and Lane, *Antibodies: A Laboratory Manual*, Cold Spring Harbor Laboratory, New York (1989); *Molec. Biology and Biotechnology: A Comprehensive Desk Reference* (Myers, R. A. (ed.), New York: VCH Publisher, Inc.); Huston et al., *Cell Biophysics*, 22:189–224 (1993); Plückthun and Skerra, *Meth. Enzymol.*, 178:497–515 (1989) and in Day, E.D., *Advanced Immunochemistry*, Second Ed., Wiley-Liss, Inc., New York, N.Y. (1990).

As used herein, the term "population" is intended to refer to a group of two or more different molecules. A population can be as large as the number of individual molecules currently available to the user or able to be made by one skilled in the art. Populations can be as small as 2–4 molecules or as large as 1013 molecules. An example where a small population can be useful is where one wishes to optimize binding affinity of a variable region or of heteromeric binding fragments by compiling beneficial differences from a small number of parent molecules having similar binding affinity into a single variable binding fragment species. An example of where large populations, including as large as $10^8$ or greater different molecules, can be desired is where all possible combinations of amino acids differences between donor and acceptor at all positions within a variable region are to be generated in order to obtain maximum diversity and increase the efficiency of compiling beneficial changes. In some embodiments, populations are between about 5 and 10 different species as well as up to hundreds or thousands of different species. The populations can be diverse or redundant depending on the intent and needs of the user. Those skilled in the art will know what size and diversity of a population is suitable for a particular application.

As used herein, the term "altered" when used in reference to an antibody variable region is intended to mean a heavy or light chain variable region that contains one or more amino acid changes in a framework region, a CDR or both compared to the parent amino acid sequence at the changed position. Where an altered variable region is derived from or composed of different donor and acceptor regions, the changed amino acid residues within the altered species are to be compared to their respective amino acid positions within the parent donor and acceptor regions. For example, a variable region containing donor CDRs grafted into an acceptor framework and containing one or more amino acid changes within the framework regions and one or more amino acid changes within the CDRs will have amino acids residues at the changed framework region positions different than the residues at the comparable positions in the acceptor framework. Similarly, such an altered variable region will have amino acid residues at the changed CDR positions different than the residues at the comparable positions in the donor CDRs.

As used herein, the term "nucleic acid" or "nucleic acids" is intended to mean a single- or double-stranded DNA or RNA molecule. A nucleic acid molecule of the invention can be of linear, circular or branched configuration, and can represent either the sense or antisense strand, or both, of a native nucleic acid molecule. The term also is intended to include nucleic acid molecules of both synthetic and natural origin. A nucleic acid molecule of natural origin can be derived from any animal, such as a human, non-human primate, mouse, rat, rabbit, bovine, porcine, ovine, canine, feline, or amphibian, or from a lower eukaryote, such as *Drosophila, C. elegans* or yeast. A synthetic nucleic acid includes, for example, chemical and enzymatic synthesis. The term "nucleic acid" or "nucleic acids" is similarly intended to include analogues of natural nucleotides which have similar functional properties as the referenced nucleic acid and which can be utilized in a manner similar to naturally occurring nucleotides and nucleosides.

As used herein, the term "coexpressing" is intended to mean the expression of two or more molecules by the same cell. The coexpressed molecules can be polypeptides or encoding nucleic acids. The coexpression can be, for example, constitutive or inducible. Such nucleic acid sequences can also be expressed simultaneously or, alternatively, regulated independently. Various combinations of these modes of coexpression can additionally be used depending on the number and intended use of the variable region encoding nucleic acids. The term is intended to include the coexpression of members originating from different populations in the same cell. For example, populations of molecules can be coexpressed where single or multiple different species from two or more populations are expressed in the same cell. A specific example includes the coexpression of heavy and light chain variable region populations where at least one member from each population is expressed together in the same cell to produce a library of cells coexpressing different species of heteromers variable region binding fragments. Populations which can be coexpressed can be as small as 2 different species within each population. Additionally, the number of molecules coexpressed from different populations also can be as large as 10⁸ or greater, such as in the case where multiple amino acid position changes of multiple framework regions or CDRs in both heavy and light chain antibody variable region populations are produced and coexpressed. Numerous different sized populations of encoding nucleic acids in between the the above ranges and greater can also be coexpressed. Those skilled in the art know, or can determine, what modes of coexpression can be used to achieve a particular goal or satisfy a desired need.

As used herein, the term "identifying" is intended to mean detecting by a qualitative or quantitative means, a variable region or altered variable of the invention by functional or biochemical properties, including, for example, binding affinity of catalytic activity.

As used herein the term "binding affinity" is intended to mean the strength of a binding interaction and therefore includes both the actual binding affinity as well as the apparent binding affinity. The actual binding affinity is a ratio of the association rate over the disassociation rate. Therefore, conferring or optimizing binding affinity includes altering either or both of these components to achieve the desired level of binding affinity. The apparent affinity can include, for example, the avidity of the interaction. For example, a bivalent heteromeric variable region binding fragment can exhibit altered or optimized binding affinity due to its valency.

As used herein, the term "optimizing" when used in reference to a variable region or a functional fragment thereof is intended to mean that the binding affinity of the variable region has been modified compared to the binding affinity of a parent variable region or a donor variable region. A variable region exhibiting optimized activity can exhibit, for example, higher affinity or lower affinity binding, or increased or decreased association or dissociation rates compared to an unaltered variable region. A variable region exhibiting optimized activity also can exhibit increased stability such as increased half-life in a particular organism. For example, an antibody activity can be optimized to increase stability by decreasing susceptibility to proteolysis. An antibody exhibiting optimized activity also can exhibit lower affinity binding, including decreased association rates or increased dissociation rates, if desired. An optimized variable region exhibiting lower affinity binding is useful, for example, for penetrating a solid tumor. In contrast to a higher affinity variable region, which would bind to the peripheral regions of the tumor but would be unable to penetrate to the inner regions of the tumor due to its high affinity, a lower affinity variable region would be advantageous for penetrating the inner regions of the tumor. As with optimization of binding affinities above, optimization of a catalytic variable region can be, for example, increased or decreased catalytic rates, disassociation constants or association constants.

As used herein, the term "substantially the same" when used in reference to binding affinity is intended to mean similar or identical binding affinities where one molecule has a binding affinity constant that is similar to another molecule within the experimental variability of the affinity measurement. The experimental variability of the binding affinity measurement is dependent upon the specific assay used and is known to those skilled in the art.

The invention provides a method for conferring donor CDR binding affinity onto an antibody acceptor variable region framework. The method consists of: (a) constructing a population of altered antibody variable region encoding nucleic acids, the population consisting of encoding nucleic acids for an acceptor variable region framework containing a plurality of different amino acids at one or more acceptor framework region amino acid positions and donor CDRs containing a plurality of different amino acids at one or more donor CDR amino acid positions; (b) expressing the population of altered variable region encoding nucleic acids, and (c) identifying one or more altered variable regions having binding affinity substantially the same or greater than the donor CDR variable region.

The process of producing human antibody forms from nonhuman species involves recombinantly splicing CDRs from a nonhuman donor antibody into a human acceptor framework region to confer binding activity onto the resultant grafted antibody, or variable region binding fragment thereof. The process of grafting, referred to as the procedure for splicing CDRs into a framework, while mechanically simple it almost always results in a grafted antibody that exhibits a substantial loss in binding affinity. Although donor and acceptor variable regions are structurally similar, the process nevertheless combines CDR binding domains with a heterologous acceptor region, resulting in a conformationally imperfect setting for the binding residues of the grafted antibody. Therefore, once the CDR-grafted antibody, or variable region binding fragment is made, it requires subsequent rounds of molecular engineering to reacquire binding affinity comparable to the donor antibody. The present invention combines these steps such that CDR grafting and binding reacquisition occur in a single simultaneous procedure. The method is also applicable to optimizing the binding affinity of an antibody, or variable region binding fragment simultaneous with CDR grafting and to optimizing an antibody or variable region binding fragment in a single procedure without including the CDR grafting process.

The methods of the invention confer or impart donor CDR binding affinity onto an antibody acceptor variable region framework in a procedure which achieves grafting of donor CDRs and affinity reacquisition in a simultaneous process. The methods similarly can be used, either alone or in combination with CDR grafting, to modify or optimize the binding affinity of a variable region. The methods for conferring donor CDR binding affinity onto an acceptor variable region are applicable to both heavy and light chain variable regions and as such can be used to simultaneous graft and optimize the binding affinity of an antibody variable region.

The methods for conferring donor CDR binding affinity onto a variable region involve identifying the relevant amino acid positions in the acceptor framework that are known or predicted to influence a CDR conformation, or that are known or predicted to influence the spacial context of amino acid side chains within the CDR that participate in binding, and then generate a population of altered variable region species that incorporate a plurality of different amino acid residues at those positions. For example, the different amino acid residues at those positions can be incorporated either randomly or with a predetermined bias and can include all of the twenty naturally occurring amino acid residues at each of the relevant positions. Subsets, including less than all of the naturally occurring amino acids can additionally be chosen for incorporation at the relevant framework positions. Including a plurality of different amino acid residues at each of the relevant framework positions ensures that there will be at least one species within the population that will have framework changes which allows the CDRs to reacquire their donor binding affinity in the context of the acceptor framework variable region.

In addition to the framework changes at selected amino acid positions, the CDRs also are altered to contain a plurality of different amino acid residue changes at all or selected positions within the donor CDRs. For example, random or biased incorporation of the twenty naturally occurring amino acid residues, or preselected subsets, are also introduced into the donor CDRs to produce a diverse population of CDR species. Including a diverse population of different CDR variant species ensures that beneficial changes in the framework positions are not neutralized by a conformationally incompatible residue in a donor CDR. Inclusion of CDR variant species into the diverse population of variable regions also allows for the generation of variant species that exhibit optimized binding affinity for a predetermined antigen.

The resultant population of CDR grafted variable regions described above will therefore contain, at the relevant framework positions and at the selected CDR positions, a species corresponding to the authentic parent amino acid residue at each position as well as a diverse number of different species which correspond to the possible combinations and permutations of the authentic parent amino acid residues together with the variant residues at each of the relevant framework and selected CDR positions. Such a diverse population of CDR grafted variable regions are screened for an altered variable region species which retains donor CDR binding activity, or optimized binding activity.

One advantage of the methods of the invention is that they do not limit the choice of acceptor variable regions applicable, or expected to be successful, for receiving CDRs from the donor molecule. For example, when choosing an acceptor region it can be desirable, or in some circumstances even required, to select an acceptor that is closely similar to the variable region amino acid sequence harboring the donor CDRs because the CDR conformation in the grafted variable region will likely be more similar to that of the donor. However, selecting similar framework region sequences between the donor and acceptor variable regions still does not provide which residues, out of the differences, actually play a role in CDR binding affinity of the grafted variable region. Selection of similar acceptor frameworks therefore only limits the number of possible residues which to investigate in order to reacquire binding affinity onto the grafted variable region. The methods of the invention circumvent this problem by producing a library of all possible or relevant changes in the acceptor framework, and then screening those variable regions, or heteromeric binding fragments thereof for species that maintain or exhibit increased binging affinity compared to the donor molecule. Therefore, the applicability is not preconditioned on the availability or search for an acceptor framework variable region similar to that of the donor.

Selection of the relevant framework amino acid positions to alter can depend on a variety of criteria well known to those skilled it the art. As described above, one criteria for selecting relevant framework amino acids to change can be the relative differences in amino acid framework residues between the donor and acceptor molecules. Selection of relevant framework positions to alter using this approach is simple and has the advantage of avoiding any subjective bias in residue determination or any inherent bias in CDR binding affinity contribution by the residue. Criteria other than relatedness of amino acid residues can be used for selecting relevant framework positions to alter. Such criteria can be used in combination with, or alternative to the selection of framework positions having divergent amino acid residues. These additional criteria are described further and similarly are well known to those skilled in the art.

Another criteria which can be used for determining the relevant amino acid positions to change can be, for example, selection of framework residues that are known to be important, or contribute to CDR conformation. For example, canonical framework residues play such a role in CDR conformation or structure. Such residues can be considered to be relevant to change for a variety of reasons, including for example, their new context of being associated with heterologous CDR sequences in the grafted variable region. Targeting of a canonical framework residue as a relevant position to change can identify a more compatible amino acid residue in context with its associated donor CDR sequence. Additionally, targeting of canonical residues can allow for the identification of residues at these positions that absorb detrimental effects to CDR structure from residues located elsewhere in the framework region.

The frequency of an amino acid residue at a particular framework position is another criteria which can be used for selecting relevant framework amino acid positions to change. For example, comparison of the selected framework with other framework sequences within its subfamily can reveal residues that occur at minor frequences at a particular position or positions. Such positions harboring less abundant residues are similarly applicable for selection as a position to alter in the acceptor variable region framework.

The relevant amino acid positions to change also can be selected, for example, based on proximity to a CDR. In certain contexts, such residues can participate in CDR conformation or antigen binding. Moreover, this criteria can similarly be used to prioritize relevant positions selected by other criteria described herein. Therefore, differentiating between residues proximal and distal to one or more CDRs is an efficient way to reduce the number of relevant positions to change using the methods of the invention.

Other criteria for selecting relevant amino acid framework positions to alter include, for example, residues that are known or predicted to reside in three-dimensional space near the antigen-CDR interface or predicted to modulate CDR activity. Similarly, framework residues that are known or predicted to contact opposite domain of the heavy ($V_H$) and light ($V_L$) chain variable region interface. Such framework positions can effect the conformation or affinity of a CDR by modulating the CDR binding pocket, antigen interaction or the $V_H$ and $V_L$ interaction. Therefore, selection of these amino acid positions as relevant for construction of the diverse population to screen can beneficially identify framework changes which replace residues having detrimental effects on CDR conformation or absorb detrimental effects of residues occurring elsewhere in the framework.

Finally, other framework residues that can be selected for alteration include amino acid positions that are inaccessible to solvent. Such residues are generally buried in the variable region and therefore capable of influencing the conformation of the CDR or $V_H$ and $V_L$ interactions. Solvent accessibility can be predicted, for example, from the relative hydrophobicity of the environment created by the amino acid side chains of the polypeptide or by known three-dimensional structural data.

In addition to selecting the relevant framework positions, the method of conferring donor CDR binding affinity onto an antibody acceptor variable region framework also incorporates changes in the donor CDR amino acid positions. As with selecting the relevant framework positions to change, there is similarly a range of possible changes that can be made in the donor CDR positions. Some or all of the possible changes that can be selected for change can be introduced into the population of grafted donor CDRs to practice the methods of the invention.

One approach is to change all amino acid positions along a CDR by replacement at each position with, for example, all twenty naturally occurring amino acids. The replacement of each position can occur in the context of other donor CDR amino acid positions so that a significant portion of the CDR maintains the authentic donor CDR sequence, and therefore, the binding affinity of the donor CDR. For example, an acceptor variable region framework targeted for relevant amino acid positions changes as described previously, can be targeted for grafting with a population of CDRs containing single position replacements at each position within the CDRs. Similarly, an acceptor variable region framework can be targeted for grafting with a population of CDRs containing more than one position changed to incorporate all twenty amino acid residues, or a fractional subset, at each set of positions within the CDRs. For example, all possible sets of changes corresponding to two, three or four or more amino acid positions within a CDR can be targeted for introduction into a population of CDRs for grafting into an acceptor variable region framework.

Single amino acid position changes are generated at each position without altering the remain amino acid positions within the CDR. A population of single position changes will contain at each position the varied amino acid residues, incorporated either randomly or with a biased frequency, while leaving the remaining positions as donor CDR residues. For the specific example of a ten residue CDR, the population will contain species having the first, second and third, continued through the tenth CDR residue, individually randomized or represented by a biased frequency of incorporated amino acid residues while the remaining non-varied positions represent the donor CDR amino acid residues. For the specific example described above, these non-varied positions would correspond to positions 2–10; 1,3–10; 1,2, 4–10, continued through positions 1–9, respectively. Therefore, the resultant population will contain species that represent all single position changes.

Similarly, double, triple and quadruple amino acid position changes can be generated for each set of positions without altering the remain amino acid positions within the CDR. For example, a population of double position changes will contain at each set of two positions the varied amino acid residues while leaving the remaining positions as donor CDR residues. The sets will correspond to, for example, positions 1 and 2, 1 and 3, 1 and 4, through the set corresponding to the first and last position of the CDR. The population will also contain sets corresponding to positions 2 and 3, 2 and 4, 2 and 5, through the set corresponding to the second an last position of the CDR. Likewise, the population will contain sets of double position changes corresponding to all pairs of position changes beginning with position three of the CDR. Similar pairs of position changes are made with the remaining sets CDR amino acid positions. Therefore, the population will contain species that represent all pairwise combinations of amino acid position changes. In a simialar fashion, populations corresponding to sets of changes representing all triple and quadruplet changes along a CDR can similarly be targeted for grafting into the variable region frameworks using the methods of the invention.

The above populations of CDR variant species can be targeted for any or all of the CDRs which constitute the binding pocket of a variable region. Therefore, an acceptor variable region framework targeted for relevant amino acid positions changes as described previously, can be targeted for the simultaneous incorporation of donor CDR variant populations at one, two or all three recipient CDR locations. The choice of which CDR or the number of CDRs to target with amino acid position changes will depend on, for example, if a full CDR grafting into an acceptor is desired or whether the method is being performed for optimization of binding affinity. Many grafting procedures will generally employ the grafting of all three CDRs, where at least one of the CDRs will contain amino acid positions changes. Generally however, all of the donor CDRs will be populations containing amino acid position changes. Converesly, and as described further below, optimization procedures can employ CDR variant populations corresponding to any or all of the CDRs within a variable region.

Another approach for selecting donor CDR amino acids to change for conferring donor CDR binding affinity onto an antibody acceptor variable region framework is to select known or readily identifiable CDR positions that are highly variable. For example, the variable region CDR 3 is generally highly variable due to genetic recombination. This region therefore can be selectively targeted for amino acid position changes during grafting procedures to ensure binding affinity reacquisition or augmentation when made together with relevant acceptor variable framework changes as described previously.

In contrast, CDR residues that appear conserved or have been empirically determined to be non-mutable by functional criteria will generally be avoided when selecting residues in the CDR to target for change. It should be noted however, that apparent non-mutable residues can nevertheless be successfully changed using the methods of the invention because the populations of altered variable regions contain from a few to many amino acid position changes in both the framework regions and in the CDR regions. As such, the CDR grafted variable regions identified by binding affinity are a result of the all the changes and therefore, all the interactions of residues introduced into a particular species. Therefore, suboptimal residues incorporated at, for example, an apparent non-mutable position can be counteracted and even augmented by amino acid substitutions elsewhere in the framework regions or in other CDRs.

Similarly, because the methods of the invention for CDR grafting, affinity reacquisition and affinity optimization employ the production and screening of diverse populations of variable region species generated from an acceptor framework and donor CDR variants, there are numerous effects on binding affinity that will occur due to the combined interactions of two or more amino acid changes within a single variable region species. For example, the affect of amino acid changes in either a framework region or CDR that are inherently beneficial can be masked or neutralized due to surrounding authentic parent residues or due to their context in a heterologous region of a grafted antibody. However, second site changes in the surrounding residues or the heterologous regions can unveil the beneficial characteristics of the latent residue or residues. Such second site changes can occur, for example, in both proximal and distal heterologous or homologous region sequences.

For example, if the beneficial residue is in a grafted CDR region, the proximal heterologous sequences would be the adjacent framework regions whereas distal heterologous regions would be framework regions separated by an adjacent CDR. In this specific example, a proximal homologous region would be the surrounding residues within the grafted CDR harboring the beneficial change whereas the remaining CDRs are examples of distal homologous regions. By analogy, the opposite would be true for a inherently beneficial residue in a framework region. Specifically, proximal homologous region sequences would be located in the same framework region and distal homologous sequences would be in any of the other framework regions. Proximal heterologous region sequences would be in the adjacent CDR or CDRs whereas nonadjacent CDRs constitute distal heterologous region sequences. Such second site effects can occur, for example, through the translation of conformational changes to the CDR binding pocket or to the framework regions.

Other effects on binding affinity that will occur due to the combined interactions of two or more amino acid changes within a single variable region species include, for example, the neutralization or augmentation of inherently detrimental changes and the augmentation of beneficial amino acid changes or the augmentation of parent residues. As with the unveiling of beneficial changes and the ability to counteract changes in apparently non-mutable residues, the neutralization and augmentation of amino acid changes within the grafted CDRs or framework region by second site changes can occur, for example, by imparting or translating conformational changes from the second site changes to the CDR binding pocket or to the framework regions. The second site changes can occur in any of the framework regions, including for example, framework regions 1 through 4 as well as in any of the three CDR regions. An advantage of the methods of the invention is that no prior information is required to assess which amino acid positions or changes can be inherently beneficial or detrimental, or which positions or changes can be further augmented by second site changes. Instead, by selecting relevant amino acid positions or subsets thereof in the acceptor variable region framework and CDRs, and generating a diverse population containing amino acid variants at these positions, combinations of beneficial changes occurring at the selected positions will be identified by screening for increased or optimized binding affinity of the CDR graft variable region. Such beneficial combinations will include the unveiling of inherently beneficial residues, neutralization of inherently detrimental residues and the augmentation of parent residues or functionally neutral changes.

Following selection of relevant amino acid positions in the framework regions and in the donor CDRs as described previously, amino acid changes at some or all of the selected positions are incorporated into encoding nucleic acids for the acceptor variable region framework and donor CDRs, respectively. Simultaneous with incorporating the encoding amino acid changes at the selected positions, the encoding nucleic acids sequences for each of the donor CDRs, including selected changes, are also incorporated into the acceptor variable region framework encoding nucleic acid to generate a population of altered variable region encoding nucleic acids.

An altered variable region of the invention will contain at least one framework position which variably incorporates different amino acid residues and at least one CDR position which variably incorporates different amino acid residues as described previously. The variability at any or all of the altered positions can range from a few to a plurality of different amino acid residues, including all twenty naturally occurring amino acids or functional equivalents and analogues thereof. The different species of the altered variable region containing the variable amino acid residues at one or more positions within the framework and CDR regions will make up the population for which to screen for an altered variable region having binding affinity substantially the same or greater than the donor CDR variable region.

Selection of the number and location of the amino acid positions to vary is flexible and can depend on the intended use and desired efficiency for identification of the altered variable region having substantially the same or greater binding affinity compared to the donor variable region. In this regard, the greater the number of changes that are incorporated into a altered variable region population, the more efficient it is to identify at least one species that exhibits substantially the same or greater binding affinity as the donor. Alternatively, where the user has empirical or actual data to the affect that certain amino acid residues or positions contribute disproportionally to binding affinity, then it can be desirable to produce a limited population of altered variable regions which focuses on changes within or around those identified residues or positions.

For example, if CDR grafted variable regions are desired, a large, diverse population of altered variable regions can include all the non-identical framework region positions between the donor and acceptor framework and all single CDR amino acid position changes. Alternatively, a population of intermediate diversity can include subsets, for example, of only the proximal non-identical framework positions to be incorporated together with all single CDR amino acid position changes. The diversity of the above populations can be further increased by, for example, additionally including all pairwise CDR amino acid position changes. In contrast, populations focusing on predetermined residues or positions which incorporate variant residues at as few as one framework and one CDR amino acid position can similarly be constructed for screening and identification of an altered antibody variable region of the invention. As with the above populations, the diversity of such focused populations can be further increased by additionally expanding on the positions selected for change to include other relevant positions in either or both of the framework and CDR regions. There are numerous other combinations ranging from few changes to many changes in either or both of the framework regions and CDRs that can additionally be employed, all of which will result in a population of altered variable regions that can be screened for the identification of at least one CDR grafted altered variable region of the invention. Those skilled in the art will know, or can determine, which selected residue positions in the framework or donor CDRs, or subsets thereof, can be varied to produce a population for screening and identification of a altered antibody of the invention given the teachings and guidance provided herein.

Simultaneous incorporation of all of the CDR encoding nucleic acids and all of the selected amino acid position changes can be accomplished by a variety of methods known to those skilled in the art, including for example, recombinant and chemical synthesis. For example, simultaneous incorporation can be accomplished by, for example, chemically synthesizing the nucleotide sequence for the acceptor variable region, fused together with the donor CDR encoding nucleic acids, and incorporating at the positions selected for harboring variable amino acid residues a plurality of corresponding amino acid codons.

One such method well known in the art for rapidly and efficiently producing a large number of alterations in a known amino acid sequence or for generating a diverse population of variable or random sequences is known as codon-based synthesis or mutagenesis. This method is the subject matter of U.S. Pat. Nos. 5,264,563 and 5,523,388 and is also described in Glaser et al. *J. Immunology* 149: 3903 (1992). Briefly, coupling reactions for the randomization of, for example, all twenty codons which specify the amino acids of the genetic code are performed in separate reaction vessels and randomization for a particular codon position occurs by mixing the products of each of the reaction vessels. Following mixing, the randomized reaction products corresponding to codons encoding an equal mixture of all twenty amino acids are then divided into separate reaction vessels for the synthesis of each randomized codon at the next position. For the synthesis of equal frequencies of all twenty amino acids, up to two codons can be synthesized in each reaction vessel.

Variations to these synthesis methods also exist and include for example, the synthesis of predetermined codons at desired positions and the biased synthesis of a predetermined sequence at one or more codon positions. Biased synthesis involves the use of two reaction vessels where the predetermined or parent codon is synthesized in one vessel and the random codon sequence is synthesized in the second vessel. The second vessel can be divided into multiple reaction vessels such as that described above for the synthesis of codons specifying totally random amino acids at a particular position. Alternatively, a population of degenerate codons can be synthesized in the second reaction vessel such as through the coupling of NNG/T nucleotides where N is a mixture of all four nucleotides. Following synthesis of the predetermined and random codons, the reaction products in each of the two reaction vessels are mixed and then redivided into an additional two vessels for synthesis at the next codon position.

A modification to the above-described codon-based synthesis for producing a diverse number of variant sequences can similarly be employed for the production of the variant populations described herein. This modification is based on the two vessel method described above which biases synthesis toward the parent sequence and allows the user to separate the variants into populations containing a specified number of codon positions that have random codon changes.

Briefly, this synthesis is performed by continuing to divide the reaction vessels after the synthesis of each codon position into two new vessels. After the division, the reaction products from each consecutive pair of reaction vessels, starting with the second vessel, is mixed. This mixing brings together the reaction products having the same number of codon positions with random changes. Synthesis proceeds by then dividing the products of the first and last vessel and the newly mixed products from each consecutive pair of reaction vessels and redividing into two new vessels. In one of the new vessels, the parent codon is synthesized and in the second vessel, the random codon is synthesized. For example, synthesis at the first codon position entails synthesis of the parent codon in one reaction vessel and synthesis of a random codon in the second reaction vessel. For synthesis at the second codon position, each of the first two reaction vessels is divided into two vessels yielding two pairs of vessels. For each pair, a parent codon is synthesized in one of the vessels and a random codon is synthesized in the second vessel. When arranged linearly, the reaction products in the second and third vessels are mixed to bring together those products having random codon sequences at single codon positions. This mixing also reduces the product populations to three, which are the starting populations for the next round of synthesis. Similarly, for the third, fourth and each remaining position, each reaction product population for the preceding position are divided and a parent and random codon synthesized.

Following the above modification of codon-based synthesis, populations containing random codon changes at one, two, three and four positions as well as others can be conveniently separated out and used based on the need of the individual. Moreover, this synthesis scheme also allows enrichment of the populations for the randomized sequences over the parent sequence since the vessel containing only the parent sequence synthesis is similarly separated out from the random codon synthesis.

Other methods well known in the art for producing a large number of alterations in a known amino acid sequence or for generating a diverse population of variable or random sequences include, for example, degenerate or partially degenerate oligonucleotide synthesis. Codons specifying equal mixtures of all four nucleotide monomers, represented as NNN, results in degenerate synthesis. Whereas partially degenerate synthesis can be accomplished using, for example, the NNG/T codon described previously. Other method well know in the art can alternatively be used such as the use of statistically predetermined, or varigated, codon synthesis which is the subject matter of U.S. Pat. Nos. 5,223,409 and 5,403,484.

Once the populations of altered variable region encoding nucleic acids have been constructed as described above, they can be expressed to generate a population of altered variable region polypeptides that can be screened for binding affinity. For example, the altered variable region encoding nucleic acids can be cloned into an appropriate vector for propagation, manipulation and expression. Such vectors are known or can be constructed by those skilled in the art and should contain all expression elements sufficient for the transcription, translation, regulation, and if desired, sorting and secretion of the altered variable region polypeptides. The vectors also can be for use in either procaryotic or eukaryotic host systems so long as the expression and regulatory elements are of compatible origin. The expression vectors can additionally included regulatory elements for inducible or cell type-specific expression. One skilled in the art will know which host systems are compatible with a particular vector and which regulatory or functional elements are sufficient to achieve expression of the polypeptides in soluble, secreted or cell surface forms.

Appropriate host cells, include for example, bacteria and corresponding bacteriophage expression systems, yeast, avian, insect and mammalian cells. Methods for recombinant expression, screening and purification of populations of altered variable regions or altered variable region polypeptides within such populations in various host systems are well known in the art and are described, for example, in Sambrook et al., *Molecular Cloning: A Laboratory Manual*, Cold Spring Harbor Laboratory, New York (1992) and in Ansubel et al., *Current Protocols in Molecular Biology*, John Wiley and Sons, Baltimore, Md. (1998). The choice of a particular vector and host system for expression and screening of altered variable regions will be known by those skilled in the art and will depend on the preference of the user. A specific example of the expression of recombinant altered variable region polypeptides is additionally described below in the Examples. Moreover, expression of diverse populations of heteromeric receptors in either soluble or cell surface form using filamentous bacteriophage vector/host systems is well known in the art and is the subject matter of U.S. Pat. No. 5,871,974.

The expressed population of altered variable region polypeptides can be screened for the identification of one or more altered variable region species exhibiting binding affinity substantially the same or greater than the donor CDR variable region. Screening can be accomplished using various methods well known in the art for determining the binding affinity of a polypeptide or compound. Additionaly, methods based on determining the relative affinity of binding molecules to their partner by comparing the amount of binding between the altered variable region polypeptides and the donor CDR variable region can similarly be used for the identification of species exhibiting binding affinity substantially the same or greater than the donor CDR variable region. All of such methods can be performed, for example, in solution or in solid phase. Moreover, various formats of binding assays are well known in the art and include, for example, immobilization to filters such as nylon or nitrocellulose; two-dimensional arrays, enzyme linked immunosorbant assay (ELISA), radioimmune assay (RIA), panning and plasmon resonance. Such methods can be found described in, for example, Sambrook et al., supra, and Ansubel et al.

For the screening of populations of polypeptides such as the altered variable region populations produced by the methods of the invention, immobilization of the populations of altered variable regions to filters or other solid substrate is particularly advantageous because large numbers of different species can be efficiently screened for antigen binding. Such filter lifts will allow for the identification of altered variable regions that exhibit substantially the same or greater binding affinity compared to the donor CDR variable region. Alternatively, if the populations of altered variable regions are expressed on the surface of a cell or bacteriophage, for example, panning on immobilized antigen can be used to efficiently screen for the relative binding affinity of species within the population and for those which exhibit substantially the same or greater binding affinity than the donor CDR variable region.

Another affinity method for screening populations of altered variable regions polypeptides is a capture lift assay that is useful for identifying a binding molecule having selective affinity for a ligand (Watkins et. al., (1997)). This method employs the selective immobilization of altered variable regions to a solid support and then screening of the selectively immobilized altered variable regions for selective binding interactions against the cognate antigen or binding partner. Selective immobilization functions to increase the sensitivity of the binding interaction being measured since initial immobilization of a population of altered variable regions onto a solid support reduces non-specific binding interactions with irrelevant molecules or contaminants which can be present in the reaction.

Another method for screening populations or for measuring the affinity of individual altered variable region polypeptides is through surface plasmon resonance (SPR). This method is based on the phenomenon which occurs when surface plasmon waves are excited at a metal/liquid interface. Light is directed at, and reflected from, the side of the surface not in contact with sample, and SPR causes a reduction in the reflected light intensity at a specific combination of angle and wavelength. Biomolecular binding events cause changes in the refractive index at the surface layer, which are detected as changes in the SPR signal. The binding event can be either binding association or disassociation between a receptor-ligand pair. The changes in refractive index can be measured essentially instantaneously and therefore allows for determination of the individual components of an affinity constant. More specifically, the method enables accurate measurements of association rates ($k_{on}$) and disassociation rates (koff).

Measurements of kon and koff values can be advantageous because they can identify altered variable regions or optimized variable regions that are therapeutically more efficacious. For example, an altered variable region, or heteromeric binding fragment thereof, can be more efficacious because it has, for example, a higher kon valued compared to variable regions and heteromeric binding fragments that exhibit similar binding affinity. Increased efficacy is conferred because molecules with higher kon values can specifically bind and inhibit their target at a faster rate. Similarly, a molecule of the invention can be more efficacious because it exhibits a lower koff value compared to molecules having similar binding affinity. Increased efficacy observed with molecules having lower koff rates can be observed because, once bound, the molecules are slower to dissociate from their target. Although described with reference to the altered variable regions and optimized variable regions of the invention including, heteromeric variable region binding fragments thereof, the methods described above for measuring associating and disassociation rates are applicable to essentially any antibody or fragment thereof for identifying more effective binders for therapeutic or diagnostic purposes.

Methods for measuring the affinity, including association and disassociation rates using surface plasmon resonance are well known in the arts and can be found described in, for example, Jonsson and Malmquist, Advances in Biosnsors, 2:291–336 (1992) and Wu et al. Proc. Natl. Acad. Sci. USA, 95:6037–6042 (1998). Moreover, one apparatus well known in the art for measuring binding interactions is a BIAcore 2000 instrument which is commercially available through Pharmacia Biosensor, (Uppsala, Sweden).

Using any of the above described screening methods, as well as others well known in the art, an altered variable region having binding affinity substantially the same or greater than the donor CDR variable region is identified by detecting the binding of at least one altered variable region within the population to its antigen or cognate ligand. Additionally, the above methods can alternatively be modified by, for example, the addition of substrate and reactants, to identify using the methods of the invention, altered variable regions having catalytic activity substantially the same or greater that the donor CDR variable region within the populations. Comparision, either independently or simultaneously in the same screen, with the donor variable region will identify those binders that have substantially the same or greater binding affinity as the donor. Those skilled in the art will know, or can determine using the donor variable region, binding conditions which are sufficient to identify selective interactions over non-specific binding.

Detection methods for identification of binding species within the population of altered variable regions can be direct or indirect and can include, for example, the measurement of light emission, radioisotopes, calorimetric dyes and fluorochromes. Direct detection includes methods that operate without intermediates or secondary measuring procedures to assess the amount of bound antigen or ligand. Such methods generally employ ligands that are themselves labeled by, for example, radioactive, light emitting or fluorescent moieties. In contrast, indirect detection includes methods that operate through an intermediate or secondary measuring procedure. These methods generally employ molecules that specifically react with the antigen or ligand and can themselves be directly labeled or detected by a secondary reagent. For example, a antibody specific for a ligand can be detected using a secondary antibody capable of interacting with the first antibody specific for the ligand, again using the detection methods described above for direct detection. Indirect methods can additionally employ detection by enzymatic labels. Moreover, for the specific example of screening for catalytic antibodies, the disappearance of a substrate or the appearance of a product can be used as an indirect measure of binding affinity or catalytic activity.

Isolated variable regions exhibit binding affinity as single chains, in the absence of assembly into a heteromeric structure with their respective $V_H$ or $V_L$ subunits. As such, populations of $V_H$ and $V_L$ altered variable regions polypeptides can be expressed alone and screened for binding affinity having substantially the same or greater binding affinity compared to the CDR donor $V_H$ or $V_L$ variable region. Alternatively, populations of $V_H$ and $V_L$ altered variable regions polypeptides can be coexpressed so that they self-assemble into heteromeric altered variable region binding fragments. The heteromeric binding fragment population can then be screened for species exhibiting binding affinity substantially the same or greater than the CDR donor variable region binding fragment. A specific example of the coexpression and self-assembly of populations $V_H$ and $V_L$ altered variable regions into hetermeric populations is described further below in the Examples.

Therefore, the invention provides a method of simultaneously grafting and optimizing the binding affinity of a variable region binding fragment. The method consists of: (a) constructing a population of altered heavy chain variable region encoding nucleic acids consisting of an acceptor variable region framework, containing donor CDRs and a plurality of different amino acids at one or more framework region and CDR amino acid positions; (b) coexpressing the populations of heavy and light chain variable region encoding nucleic acids to produce diverse combinations of heteromeric variable region binding fragments, and (c) identifying one or more heteromeric variable region binding fragments having affinity substantially the same or greater than the donor CDR heteromeric variable region binding fragment.

The invention additionally provides a method of optimizing the binding affinity of an antibody variable region. The consists of: (a) constructing a population of antibody variable region encoding nucleic acids, said population comprising two or more CDRs containing a plurality of different amino acids at one or more CDR amino acid positions; (b) expressing said population of variable region encoding nucleic acids, and (c) identifying one or more variable regions having binding affinity substantially the same or greater than the donor CDR variable region.

The methods described above, for conferring donor CDR binding affinity onto an antibody acceptor variable region framework and for simultaneously grafting and optimizing the binding affinity of a heteromeric variable region binding fragment, can additionally be employed to modify or optimize the binding affinity of a variable region or a heteromeric variable region binding fragment. Similar to the previously described methods, the method for modifying or optimizing binding affinity involves the selection of relevant amino acid positions and the construction, expression and screening of variable region populations containing variable amino acid residues at all or a fraction of the selected positions. However, for optimization of binding affinity it is not necessary to vary amino acid positions in the framework regions. Instead, all that is required is to alter one or more amino acid positions in two or more CDR regions. Changing the CDR amino acid residues directly effects the binding affinity. Once a population containing variable amino acid residues incorporated in two or more CDRs is produced, all that is necessary is to screen the population for species that contain the desired binding affinity modification. All of the criteria for selecting relevant amino acid positions described previously are applicable for use in this mode of the method. Therefore, the methods for modifying or optimizing the binding affinity of a variable region or a heteromeric variable region binding fragment by altering one or more amino acid positions in two or more CDR regions are applicable to essentially any variable region, grafted variable region as well as applicable to the altered and optimized variable regions of the invention.

Moreover, by incorporating variable amino acid residues in two or more CDRs when employing the methods conferring donor CDR binding affinity onto an acceptor framework, this method of modifying binding affinity is therefore useful for simultaneously optimizing the binding affinity of a grafted antibody. Employing the methods for simultaneously grafting and optimizing, or for optimizing, it is possible to generate heteromeric variable region binding fragments having increases in affinities of greater than 5-, 8- and 10-fold. In particular, heteromeric variable region binding fragments can be generated having increases in affinities of greater than 12-, 15- 20- and 25-fold as well as affinities greater than 50-, 100- and 1000-fold compared to the donor or parent molecule.

Additionally, the methods described herein for optimizing are also are applicable for producing catalytic heteromeric variable region fragments or for optimizing their catalytic activity. Catalytic activity can be optimized by changing, for example, the on or off rate, the substrate binding affinity, the transition state binding affinity, the turnover rate (kcat) or the Km. Methods for measuring these characteristics are well known in the art. Such methods can be employed in the screening steps of the methods described above when used for optimizing the catalytic activity of a heteromeric variable region binding fragment.

The methods for conferring donor CDR binding affinity onto an antibody acceptor variable region framework described previously are applicable for use with essentially any distinguishable donor and acceptor pair. Many applications of the methods will be for the production and optimization of variable region binding fragments having human acceptor frameworks due to the therapeutic importance of such molecules in the treatment of human diseases. However, the method are applicable for conferring donor CDR binding affinity onto an acceptor originating from the same or a divergent species as the CDR donor variable region so long as the framework regions between the donor and acceptor variable regions are distinct. Therefore, the invention included altered variable regions having acceptor frameworks derived from human, mouse, rat, rabbit, goat and chicken, for example.

Additionally, the methods for conferring donor CDR binding affinity onto an antibody acceptor variable region framework are applicable for grafting CDRs as described by Kabat et al., supra, Chothia et al., supra or MacCallum et al., supra. The methods similarly can be used for grafting into an acceptor framework overlapping regions or combinations of CDR as described by these authors. Generally, the methods will graft variable region CDRs by identifying the boundries described by one of the CDR definitions known in the art and set forth herein. However, because the methods are directed to constructing and screening populations of CDR grafted altered variable regions which incorporate relevant amino acid position changes in both the framework and CDR regions, and such variations can, for example, compensate or augment amino acid changes elsewhere in the variable region, the exact boundry of a particular CDR or set of variable region CDRs can be varied. Therefore, the exact CDR region to graft, whether it is the region described by Kabat et al., Chothia et al. or MacCallum et al., or any combination thereof, will essentially depend on the preference of the user.

Similarly, the methods described previously for optimizing the binding affinity of an antibody also are applicable for use with essentially any variable region for which an encoding nucleic acid is, or can be made available. As with the methods for conferring donor CDR binding affinity, many applications of the methods for optimizing binding affinity will be for modifying the binding affinity of CDR grafted variable regions having human frameworks. Again, such molecules are significantly less antigenic in human patients and therefore therapeutically valuable in the treatment of human diseases. However, the methods of the invention for optimizing the binding affinity of a variable region are applicable to all species of variable regions. Therefore, the invention includes binding affiity optimization of variable regions derived from human, mouse, rat, rabbit, goat and chicken, for example.

The methods of the invention have been described with reference to variable regions and heteromeric variable region binding fragments. Given these descriptions and teaching herein, those skilled in the art will understand that all of such methods are applicable to whole antibodies and functional fragments thereof as well as to regions and functional domains other than the antigen binding variable region of antibodies. Moreover, the methods described herein are further applicable to molecules other than antibodies, variable regions and other antibody functional domains. Given the teachings of the invention, those skilled in the art will know how to apply the methods of simultaneously constructing hybrid molecules and maintaining or optimizing the binding affinity or catalytic activity of a target molecule, as well as how to apply the methods of optimizing the binding affinity or catalytic activity to a variety of different types and classes of polypeptides and proteins.

The methods for optimizing the binding affinity of an antibody variable region can include the selection of relevant acceptor framework and donor CDR amino acid positions to be altered. Amino acid residues selected for alteration during binding affinity optimization are typically amino positions predicted to be relatively important for structure or function. Criteria that can be used for identifying amino positions to be altered include, for example, conservation of amino acids among polypeptide subfamily members and knowledge that particular amino acids are predicted to be important in polypeptide conformation or structure, as described above. Alternatively, potentially important framework residues that differ between acceptor framework and donor CDR can be characterized without structural information by synthesizing and expressing a combinatorial antibody library that contains all possible combinations of amino acids in framework positions to be optimized.

The invention provides a method for identifying one or more functional amino acid positions of a polypeptide. The method consists of (a) constructing a population of nucleic acids encoding a population of altered polypeptides containing substitutions of one or more amino acid positions within a polypeptide; (b) expressing the population of nucleic acids; (c) identifying nucleic acids encoding altered polypeptides having a functional activity of the polypeptide; (d) sequencing a subset of nucleic acids encoding altered polypeptides having a functional activity, and (e) comparing an amino acid position in a polypeptide corresponding to an amino acid position in the subset of altered polypeptides wherein an amino acid position exhibiting a biased representation of amino acid residues indicates a functional amino acid position in the polypeptide.

The method of the invention directed to identifying a functional amino acid position in a polypeptide involves substituting one or more amino acid positions in a polypeptide with a plurality of amino acid residues, as described previously for optimizing the binding affinity of an antibody, and identifying altered polypeptides having an activity that is substantially the same or greater than the parent polypeptide. Functional amino acid positions identified using the methods of the invention are amino acid positions important for a conformation, functional activity or structure of a polypeptide. Functional activities of a polypeptide can include, for example, binding affinity to a substrate, ligand, or other interacting molecule, and catalytic activity.

The identification of functional amino acid positions in a polypeptide involves constructing a population of nucleic acids encoding a population of altered polypeptides containing amino acid substitutions at specific amino acid positions. Substituted amino acids include all twenty naturally occurring amino acid residues or a subset of amino acid residues, as described previously in detail. Nucleic acid populations can be constructed by any method known in the art and as described previously. A population of nucleic acids encoding altered polypeptides is expressed in an appropriate host cell, and a functional activity of altered polypeptides is detected and compared with that of the polypeptide. Any method known in the art that is appropriate for determining a polypeptide functional activity can be used to compare polypeptide and altered polypeptide functional activities.

A subset of nucleic acids encoding altered polypeptides having a functional activity that is substantially the same or greater than that of the polypeptide is sequenced. A subset can include a few molecules to many members constituting the population of nucleic acids encoding altered polypeptides. For example, a subset can consist of about 2–5, 6–10, 10–20, and 21 or greater members of the population. The actual number sequenced will vary with the total size of the nucleic acid population. Generally, however, a subset of about 15–25 and typically about 20 members is sufficient in order to identify functional amino acids.

Amino acid residues at substituted positions in the polypeptide are compared to the corresponding position in altered polypeptides. An amino acid position that contains the same amino acid or a conservative substitution among the population of altered polypeptides exhibits biased representation of that amino acid residue. Biased representation indicates that a particular amino acid is required for polypeptide function. Amino acid positions that are biased are therefore considered important for functional activity of a polypeptide. Amino acid positions that contain a variety of substituted amino acids are unbiased and considered not important or less important for a polypeptide function.

The method of identifying an amino acid position important for polypeptide function is useful for a variety of applications, such as, for example, the determination of a consensus sequence of amino acids important for a polypeptide functional activity. A consensus sequence is useful for the optimization of a polypeptide function because amino acid positions determined to be important for functional activity can be unaltered while amino acid positions not important for activity can be varied. Polypeptide functions that can be optimized using the method of the invention include, for example, catalytic activity, polypeptide conformation and binding affinity.

The identification of a functional amino acid position in a polypeptide can be applied to determining a consensus sequence of amino acids that impart a particular activity to a polypeptide. For example, a consensus sequence that provides a catalytic activity to an enzyme can be determined using the methods of the invention. To identify amino acid positions that are important or critical to catalytic activity of an enzyme, one or more of amino acid positions are substituted with a plurality of amino acid substitutions, as described previously. A nucleic acid population encoding altered enzyme polypeptides is constructed and expressed in host cells. The catalytic activity of altered enzymes is measured and compared with a parent enzyme or other catalytically active form of the enzyme.

Nucleic acids encoding a subset of altered enzyme polypeptides identified by functional activity are sequenced, and the amino acid sequences of altered polypeptides are compared. Amino acid positions that contain a particular amino acid or a conservative substitution are determined to be important for a catalytic activity of the enzyme. A sequence of amino acids determined to be biased in a polypeptide can thus provide a consensus sequence that defines amino acid positions required for catalytic activity. A consensus sequence of residues important for various aspects of catalytic activity such as, for example, substrate binding, proper active site conformation, and co-factor binding can be identified using the methods of the invention by measuring enzyme catalytic activity, as described above.

Similarly, a consensus sequence associated with a particular conformation of a polypeptide can be determined using the method of the invention in essentially the same manner as described above for polypeptide catalytic activity. The amino acid positions that have functional roles in a polypeptide conformation can be determined so long as a particular conformation state can be detected and compared between a polypeptide and an altered polypeptide. For example, a consensus sequence of a polypeptide conformation that confers a particular functional activity to a polypeptide or a particular structural feature to a polypeptide can be determined using the methods of the invention. A structural feature can include, for example, the exposure of a certain amino acid on the surface of a polypeptide.

A consensus sequence of amino acid positions in a polypeptide important for binding affinity can also be determined using the methods of the invention. The binding affinities of polypeptides include, for example, the binding affinity between two or more polypeptides in a protein—protein interaction and the binding affinity between a polypeptide and a substrate. For example, a consensus sequence for the binding affinity of an antibody for an antigen can be determined, and can be applied to the process of antibody humanization.

The identification of a functional amino acid position in a polypeptide can be applied to determining the consensus sequence for a humanized version of an antibody that preserves the binding activity of the parent antibody. For example, a library containing all possible combinations of human template and murine parent antibody residues in a selected number of amino positions can be synthesized by method known in the art, for example, using codon-based mutagenesis as described previously. Framework polypeptides containing amino acid substitutions can then be screened by functional binding to identify altered framework polypeptides that have a binding affinity substantially the same as the parent antibody. Of the amino acid positions altered, only a small percentage of framework positions are typically critical for antibody binding activity. Therefore, a low throughput screening method of identifying active humanized framework variants can be used. Sequencing of nucleic acids encoding humanized frameworks displaying a functional activity of the parent antibody is then used to identify altered polypeptides having significant bias toward murine human residues. Thus, a consensus humanization sequence for maintaining full binding activity of an antibody can be prepared by using murine CDRs grafted onto a human template on which amino acid positions are changed to the corresponding residue determined to be important for binding activity.

It is understood that modifications which do not substantially affect the activity of the various embodiments of this invention are also included within the definition of the invention provided herein. Accordingly, the following examples are intended to illustrate but not limit the present invention.

EXAMPLE I

Simultaneous Humanization and Affinity Maturation of an Anti-CD40 Antibody

This example shows the simultaneous humanization and affinity maturation of the murine mAb 40.2.220, directed against the CD40 receptor.

The CD40 receptor is a potential therapeutic target for several diseases. For example, the interaction of the CD40 receptor and its ligand, gp39, serves a critical role in both humoral and cell-mediated immune responses (Foy et. al., (1996)). Immunological rejection of organs from genetically non-identical individuals, termed graft-versus-host-disease (GVHD), is mediated through T cell-dependent mechanisms. In vivo administration of an anti-gp39 mAb blocks GVHD in mice and inhibits many of the GVHD-associated phenomena (Durie et. al., 1994)), providing evidence that the CD40/gp39 interaction plays a critical role in the development of GVHD. More recently, inhibition of the CD40/gp39 interaction in vivo in hyperlipidemic mice fed a high cholesterol diet limited atherosclerosis, suggesting that CD40 signalling may also play a role in atherogenesis (Mach et. al., (1998)). In addition, the CD40 receptor is overexpressed on hematologic malignancies (Uckun et. al., 1990)) and certain carcinomas (Stamenkovic et. al., (1989)) and thus, may serve as a target for cytotoxic agents. An anti-CD40 single chain antibody-toxin fusion was cytotoxic against CD40-expressing malignant cells in vitro (Francisco et. al., (1995)) and was efficacious in treating human non-Hodgkin's lymphoma xenografted SCID mice (Francisco et. al., (1997)).

Codon-based mutagenesis (Glaser et. al., (1992)) was used to create libraries of LCDR3, HCDR3 and framework region variants of mAb 40.2.220 sequences. Libraries composed of framework region variants alone and in combination with HCDR3 variants and with HCDR3 and LCDR3 variants together were screened for high affinity variants. It was demonstrated that in combination higher affinity variants were obtained than those obtained when codon-based mutagenesis was applied independently thus showing (1) higher affinity variants that could only be obtained by the use of codon-based mutagenesis simultaneously on disparate regions of the mAb and (2) the use of codon-based mutagenesis to uncover potential direct interactions between disparate regions of a mAb.

A vector for the production of a chimeric anti-CD40 murine mAb 40.2.220 was constructed. Based on the sequence of anti-CD40 murine mAb 40.2.220 (provided by Dr. D. Hollenbaugh, Bristol-Myers Squibb, Princeton, N.J.) overlapping oligonucleotides encoding $V_H$ and $V_L$ (69–75 bases in length) were synthesized and purified. The variable H and L domains were synthesized separately by combining 25 pmol of each of the overlapping oligonucleotides with Pfu DNA polymerase (Stratagene) in a 50 µl PCR reaction consisting of 5 cycles of: denaturing at 94° C. for 20 sec, annealing at 50° C. for 30 sec, ramping to 72° C. over 1 min, and maintaining at 72° C. for 30 sec. Subsequently, the annealing temperature was increased to 55° C. for 25 cycles. A reverse primer and a biotinylated forward primer were used to further amplify 1 µl of the fusion product in a 100 µl PCR reaction using the same program. The products were purified by agarose gel electrophoresis, electroeluted, and phosphorylated by T4 polynucleotide kinase (Boehringer Mannheim) and were then incubated with streptavidin magnetic beads (Boehringer Mannheim) in 5 mM Tris-Cl, pH 7.5, 0.5 mM EDTA, 1 M NaCl, and 0.05% Tween 20 for 15 min at 25° C. The beads were washed and the non-biotinylated, minus strand DNA was eluted by incubating with 0.15 M NaOH at 25° C. for 10 min. Chimeric anti-CD40 Fab was synthesized in a modified M131X104 phage vector (Kristensson et. al., 1995)), termed M131X104CS, by hybridization mutagenesis (Rosok et. al., (1996); Kunkel, (1985)) using the $V_H$ and $V_L$ oligonucleotides in 3-fold molar excess of the uridinylated vector template. The M131X104 vector was modified by replacing cysteine residues at the end of the kappa and γ1 constant regions with serine. The reaction was electroporated into DH10B cells and titered onto a lawn of XL-1 Blue.

The murine anti-CD40 mAb variable region framework sequences were used to identify the most homologous human germline sequences. The H chain framework residues were 74% identical to human germline VH7 (7–4.1) and JH4 sequences while the L chain was 75% identical to the corresponding human germline VKIII (L6) and JK4 sequences. Alignment of the H and L chain variable sequences is shown in FIG. 1. CDR residues, as defined by Kabat et. al. (1977, 1991), are underlined and were excluded from the homology analysis. Differences in sequence are indicated by vertical lines and framework positions characterized in the combinatorial expression library are marked with an asterisk. Framework residues that differed between the murine mAb and the human templates were assessed individually.

Based on structural and sequence analysis, antibody CDRs with the exception of HCDR3 display a limited number of main chain conformations termed canonical structures (Chothia & Lesk, (1987); Chothia et. al., (1989)). Moreover, certain residues critical for determining the main chain conformation of the CDR loops have been identified (Chothia & Lesk, (1987); Chothia et. al., (1989)). Canonical framework residues of murine anti-CD40 were identified therefore, and it was determined that amino acids at all critical canonical positions within the H and L chain frameworks of the human templates were identical to the corresponding murine residues.

Surface-exposed murine amino acids not normally found in human antibodies are likely to contribute to the immunogenicity of the humanized mAb (Padlan, (1991)). Therefore, framework residues differing between murine anti-CD40 and the human templates were analyzed and based on solvent exposure were predicted to be buried or located on the surface of the antibody (Padlan, (1991)). Solvent-exposed framework residues distal to the CDRs were not expected to contribute to antigen binding significantly and thus, with the exception of two H chain residues all were changed to the corresponding human amino acid to decrease potential immunogenicity. H chain residues 28 and 46 were predicted to be solvent exposed. However, H28 is located within the HCDR1 region as defined by Chothia & Lesk (1987) and potentially interacts with the antigen. In addition, the lysine at H46 in the murine mAb is somewhat unusual and significantly different from the glutamic acid of the human template. Therefore, the murine and human residues at H28 and H46 were expressed in the combinatorial library (FIG. 1, asterisks).

The remaining differing framework residues, all predicted to be mostly buried within the antibody, were evaluated for: (1) proximity to CDRS, (2) potential to contact the opposite domain in the $V_K$–$V_H$ interface, (3) relatedness of the differing amino acids, and (4) predicted importance in modulating CDR activity as defined by Studnicka et. al., (1994). The majority of L chain framework differences in buried residues were related amino acids at positions considered not likely to be directly involved in the conformation of the CDR. However, L49 is located adjacent to LCDR2, potentially contacts the $V_H$ domain, is unrelated to the human residue, and may be involved in determining the conformation of LCDR2. For these reasons, the murine and human amino acids at L49 were both expressed in the combinatorial framework library (FIG. 1, asterisk).

Analysis of the murine H chain sequence and the human template was performed. Residue H9 is a proline in the murine mAb while the human template contains an unrelated serine residue. Position H9 can also play a role in modulating the conformation of the CDR and thus, was selected as a combinatorial library site (FIG. 1, asterisks). The remaining buried framework residues that differed between murine anti-CD40 and the H chain template were at framework positions 38, 39, 48, and 91. Murine anti-CD40 mAb contained glutamine and glutamic acid at H38 and H39, respectively, while the human template contained arginine and glutamine. Residue H38 is in proximity to the HCDR1, the glutamine→arginine change is non-conserved, and expression of glutamine at this site in murine Abs is somewhat unusual. Similarly, glutamic acid→glutamine is a non-conservative difference for buried amino acids, H39 is a potential $V_K$ contact residue, and glutamic acid is somewhat unusual in murine mAbs. Residue H48 is in close proximity to HCDR2 and H91 is predicted to be a high risk site (Studnicka et. al., (1994); Harris & Bajorath, (1995)) that potentially contacts the $V_K$ domain. Thus, both murine and human residues were expressed at H38, 39, 48, and 91 (FIG. 1, asterisks).

The combinatorial framework library (Hu I) was synthesized by the same method used to construct the chimeric anti-CD40, with modifications. Overlapping oligonucleotides encoding the framework regions of the H and L variable domains of the human template and the murine anti-CD40 CDRs as defined by Kabat et. al. (1977, 1991) were synthesized. Among these, degenerate oligonucleotides encoding both the murine and the human amino acids at seven $V_H$ and one $V_K$ framework position as selected above were synthesized (FIG. 1 residues marked with asterisk). All of these sites were characterized by synthesizing a combinatorial library that expressed all possible combinations of the murine and human amino acids found at these residues. The total diversity of this library, termed Hu I, was $2^8$ or 256 variants (Table I).

The Hu I combinatorial library was first screened by an ELISA that permits the rapid assessment of the relative affinities of the variants (Watkins et. al., (1997)). Briefly, microtiter plates were coated with 5 µg/ml goat anti-human kappa (Southern Biotechnology) and blocked with 3% BSA in PBS. Certain Fabs were cloned into an expression vector under the control of the arabinose-regulated BAD promoter.

In addition, a six-histidine tag was fused to the carboxyl-terminus of the H chain to permit purification with nickel-chelating resins. Purified Fab was quantitated as described (Watkins et. al., 1997). Next, 50 µl Fab from the *Escherichia coli* culture supernatant or from the cell lysate, was incubated with the plate 1 h at 25° C., the plate was washed three times with PBS containing 0.1% Tween 20, and incubated with 0.1 µg/ml CD40-Ig in PBS containing 1% BSA for 2 h at 25° C. The plate was washed three times with PBS containing 0.1% Tween 20 and goat anti-mouse $IgG_{2b}$-alkaline phosphatase conjugate diluted 3000-fold in PBS containing 1% BSA was added for 1 h at 25° C. The plate was washed three times with PBS containing 0.1% Tween 20 and was developed as described (Watkins et. al., (1997)).

Although variants that bind the target antigen with affinities comparable to, or better than the chimeric Fab were identified, the majority of Hu I clones screened were less active than the chimeric anti-CD40 Fab. Approximately 6% of randomly selected Hu I variants displayed binding activities comparable to the chimeric Fab (data not shown). The identification of multiple Hu I variants with activity comparable to the chimeric CD40 is consistent with the interpretation that the most critical framework residues were included in the combinatorial library.

The kinetic constants for the interaction between CD40 and the anti-CD40 variants were determined by surface plasmon resonance (BIAcore). CD40-Ig fusion protein was immobilized to a (1-ethyl-3-[3-dimethylaminopropyl]-carbodiimide hydrochloride) and N-hydroxysuccinimide-activated sensor chip CM5 by injecting 8 µl of 10 µg/ml CD40-Ig in 10 mM sodium acetate, pH 4. CD40-Ig was immobilized at a low density (~150 RU) to prevent rebinding of Fabs during the dissociation phase. To obtain association rate constants ($k_{on}$), the binding rate at six different Fab concentrations ranging from 25–600 nM in PBS was determined at a flow rate of 20 µl/min. Dissociation rate constants ($k_{off}$) were the average of six measurements obtained by analyzing the dissociation phase. Sensorgrams were analyzed with the BIAevaluation 3.0 program. $K_d$ was calculated from $K_d = k_{off}/k_{on}$. Residual Fab was removed after each measurement by prolonged dissociation.

FIG. 2A shows bacterially-expressed chimeric anti-CD40 Fab and certain variants from each of the libraries were titrated on immobilized antigen. Chimeric (filled circles), Hu I-19C11 (open circles), Hu II-CW43 (open squares), Hu III-2B8 (filled triangles), and an irrelevant (filled squares) Fab were released from the periplasmic space of 15 ml bacterial cultures and serial dilutions were incubated with CD40-Ig antigen immobilized on microtiter plates. See below for description of HuII and HuIII libraries. Antibody binding was quantitated as described above. These measurements confirm the identification of multiple variants with enhanced affinity. For example, clone 19C11 binds the CD40 receptor with higher affinity than the chimeric Fab, as demonstrated by the shift in the titration profile (compare open circles with filled circles). DNA sequencing of 34 of the most active clones led to the identification of 24 unique framework combinations, each containing 2–6 murine framework residues (data not shown).

LCDR3 and HCDR3 contact antigen directly, interact with the other CDRs, and often affect the affinity and specificity of antibodies significantly (Wilson & Stanfield, (1993); Padlan, (1994)). In addition, the conformation of LCDR3 and HCDR3 are determined in part by certain framework residues. Therefore, to identify the most active antibody it could be beneficial to construct combinatorial libraries that optimize the third CDR of the H and L chains in conjunction with selecting the most active framework.

Codon-based mutagenesis (Glaser et. al., (1992)) was used to synthesize oligonucleotides that introduce mutations at every position in HCDR3, one at a time, resulting in the expression of all 20 amino acids at each CDR residue from $Ser^{95}$-$Tyr^{102}$ (FIG. 1, underlined). Briefly, for library construction, the overlapping oligonucleotides encoding the framework library and non-library murine CDR were combined with 25 pmol of the oligonucleotides encoding mutated HCDR3. The pool of oligonucleotides encoding the HCDR3 library was mixed with the overlapping oligonucleotides encoding the combinatorial framework and other CDRs to generate a framework/HCDR3 library. The diversity of this library, termed Hu II, was $1.1 \times 10^5$ (Table I).

The CDR residues selected for mutagenesis of LCDR3 were $Gln^{89}$-$Thr^{97}$ (FIG. 1, underlined). Oligonucleotides encoding LCDR3 were designed to mutate a single CDR residue in each clone as described above for HCDR3. Oligonucleotides encoding the LCDR3, HCDR3, and the combinatorial framework were used to create a framework/HCDR3/LCDR3 library, termed Hu III. The large number of framework/CDR3 combinations resulted in a library with a complexity of $3.1 \times 10^7$ (Table I).

TABLE I

Summary of phage-expressed anti-CD40 antibody libraries.

| Library | Library Positions | Size* | Screened† |
|---|---|---|---|
| Hu I | framework | 256 | $2.4 \times 10^3$ |
| Hu II | framework, HCDR3 | $1.1 \times 10^5$ | $2.0 \times 10^6$ |
| Hu III | framework, HCDR3, LCDR3 | $3.1 \times 10^7$ | $5.5 \times 10^5$ |

*Number of unique clones based on DNA sequence. Thirty-two codons are used to encode all 20 amino acids at each CDR position.

An additional library (Hu IV) was synthesized to further optimize the best variant (clone F4) identified from the Hu III library. Oligonucleotides encoding LCDR3, designed to mutate a single CDR residue in each clone, were synthesized by introducing NN(G/T) at each position (Glaser et. al., (1992)) and were annealed to uridinylated F4 template (Kunkel, (1985)) which already contained a $^{96}R \rightarrow W$ mutation in LCDR3.

Combining mutations in LCDR3 and/or HCDR3 with the framework library increased the potential diversity of humanized anti-CD40 variants from 256 to greater than $10^7$. In order to screen these larger libraries more efficiently a modified plaque lift assay, termed capture lift, was used (Watkins et. al., (1997)). Briefly, nitrocellulose filters (82-mm) were coated with goat anti-human kappa, blocked with 1% BSA, and were applied to an agar plate containing the phage-infected bacterial lawn. In the initial screen, phage were plated at $10^5$ phage/100-mm plate. After the capture of phage-expressed anti-CD40 variant Fabs, the filters were incubated 3 h at 25° C. with 5 ng/ml CD40-Ig in PBS containing 1% BSA. The filters were rinsed four times with PBS containing 0.1% Tween 20 and were incubated with goat anti-mouse $IgG_{2b}$-alkaline phosphatase conjugate (Southern Biotechnology) diluted 3000-fold in PBS containing 1% BSA for 1 h at 25° C. The filters were washed four times with PBS containing 0.1% Tween 20 and were developed as described (Watkins et. al., (1998)). To isolate individual clones, positive plaques from the initial screen were picked, replated at lower density (<$10^3$ phage/100-mm plate), and were screened by the same approach. Because the filters were probed with antigen at a concentration substantially below the $K_d$ of the Fab only variants displaying enhanced affinity were detectable. Multiple clones displaying higher affinities were identified following the screening of >$10^6$ variants from Hu II and >$10^5$ variants from the Hu III library using 82-mm filters containing $10^5$ variants per filter (Table I). Titration of the variants on immobilized CD40-Ig verified that multiple clones displayed affinities greater than the chimeric and humanized Fab (FIG. 2A, compare open squares, filled triangles with circles).

The framework/CDR mutations that conferred enhanced affinity were identified by DNA sequencing. Single-stranded DNA was isolated and the H and L chain variable region genes were sequenced by the fluorescent dideoxynucleotide termination method (Perkin-Elmer, Foster City, Calif.). Unique variable region sequences were identified in 10/13 Hu II variants and 4/5 Hu III variants. Both the Hu II and Hu III variants contained 1–5 murine framework residues and 0–2 CDR3 mutations. Representative examples are summarized in Table II. The affinities of bacterially-expressed chimeric Fab and certain variants from each of the libraries were characterized more thoroughly using surface plasmon resonance measurements to determine the association and dissociation rates of purified Fab with immobilized CD40-Ig as described above.

Chimeric anti-CD40 had a dissociation constant $K_d$=48.3 nM and, consistent with the screening results, the variants all displayed higher affinities with $K_d$ ranging from 0.24 nM to 10.5 nM (Table II). Further optimization of LCDR30f Hu III clone F4 resulted in the identification of a higher affinity ($K_d$=0.1 nM) clone, L3.17, which contained a $^{94}$F→Y mutation. The improved affinities of the anti-CD40 variants were predominantly the result of slower dissociation rates. However, the association rates of most variants were also enhanced, increasing by as much as ≈3-fold (1.2 vs. 3.2×10$^6$ M$^{-1}$s$^{-1}$ for chimeric anti-CD40 and clone L3.17, respectively).

TABLE II

Simultaneous optimization of framework and CDR residues.

| Library | Clone | Kd (nM) | Murine Fr Residues* | CDR Mutations |
|---|---|---|---|---|
|  | chimeric | 48.3 | (43) | 0 |
| Hu I | 19C11 | 42.4 | (2) H28, 48 | 0 |
|  | 1H11 | 53.4 | (4) H9, 28, 91, L49 | 0 |
|  | 9A3 | 43.9 | (3) H9, 28, 91 | 0 |
| Hu II | CW43 | 10.53 | (3) H9, 28, 91 | HCDR3, $^{101}$A → R |
|  | Y49K† | 53.4 | (4) H9, 28, 91, L49 | HCDR3, $^{101}$A → R |
|  | 2B12 | 4.67 | (5) H9, 28, 38, 46, 48 | HCDR3, $^{101}$A → K |
| Hu III | 2B12 | 4.67 | (5) H9, 28, 38, 46, 48 | HCDR3, $^{101}$A → K |
|  | 2B8 | 2.81 | (1) H2B | HCDR3, $^{101}$A → K; LCDR3, $^{96}$R → Y |
|  | F4 | 0.24 | (1) H28 | HCDR3, $^{101}$A → K; LCDR3, $^{96}$R → W |
| Hu IV | L3.17 | 0.10 | (1) H28 | HCDR3, $^{101}$A → K; LCDR3, $^{94}$F → Y; LCDR3, $^{96}$R → W |

*The number of murine framework residues that differ from the most homologous human germline sequence based on definition of CDRs per Kabat et. al. (1977, 1991) are indicated in parentheses. Differing murine framework residues retained in the humanized versions are located predominantly on the H chain (H) at the indicated positions, Hu I clone 1H11 and the CW43 derivative, clone Y49K, contan a single differing L chain (L) framework residue at position 49.
†Clone Y49K was created by site-directed mutagenesis of clone CW43. The four clones within the shaded boxed region, 1H11, 9A3, CW43, and Y49K, were characterized to demonstrate the co-operative interaction between L chain framework residue tyr$^{49}$ (human) and HCDR3 residue arg$^{101}$.

The variants displaying enhanced affinity were tested for their ability to block the binding of gp39 ligand to the CD40 receptor. Immulon II microtiter plates were coated with 2 μg/ml anti-murine CD8 to capture sgp39 fusion protein which expresses the CD8 domain. The plates were rinsed once with PBS containing 0.05% Tween 20, and were blocked with 3% BSA in PBS. The plate was washed once with PBS containing 0.05% Tween 20 and was incubated with cell culture media containing saturating levels of sgp39 for 2 h at 25° C. Unbound sgp39 was aspirated and the plate was washed two times with PBS containing 0.05% Tween 20. Next, 25 μl of purified variant Fabs diluted serially 3-fold in PBS was added followed by 25 μl of 4 μg/ml CD40-human Ig in PBS. The plates were incubated 2 h at 25° C. and were washed three times with PBS containing 0.05% Tween 20. Bound CD40-human Ig was detected following a 1 h incubation at 25° C. with goat F(ab')$_2$ anti-human IgG Fcγ-specific horseradish peroxidase conjugate (Jackson) diluted 10,000-fold in PBS. The plate was washed four times with PBS containing 0.05% Tween 20 and binding was quantitated colorimetrically by incubating with 1 mg/ml o-phenylenediamine dihydrochloride and 0.003% hydrogen peroxide in 50 mM citric acid, 100 mM Na$_2$HPO$_4$, pH 5. The reaction was terminated by the addition of H$_2$SO$_4$ to a final concentration of 0.36 M and the absorbance at 490 nm was determined. FIG. 2B shows purified variants were tested for their ability to inhibit sgp39 binding to CD40-Ig. The ligand for the CD40 receptor, gp39, was captured in a microtiter plate and subsequently, varying amounts of purified chimeric (filled circles), Hu II-CW43 (open squares), Hu III-2B8 (filled triangles), Hu II/III-2B12 (open triangles), and irrelevant (filled squares) Fab were co-incubated with 2 μg/ml CD40-human Ig on the microtiter plate. The variants all inhibited the binding of soluble CD40-Ig fusion protein to immobilized gp39 antigen in a dose-dependent manner that correlated with the affinity of the Fabs. For example, one of the most potent inhibitors of ligand binding to CD40-Ig fusion protein was variant 2B8, which was also one of the variants with the highest affinity for CD40. Variant 2B8 displayed ≈17-fold higher affinity for CD40 than did the chimeric Fab and inhibited ligand binding ≈7-fold more effectively.

Screening of the Hu I library identified two variants that were similar or identical in framework sequence to the Hu II clone CW43 but displayed 5-fold lower affinities (Table II, clones 1H11 and 9A3). Clone 9A3 has an identical framework structure while 1H11 contained the murine lysine framework residue at L chain position 49. Sequence comparisons and site-directed mutagenesis studies (data not shown) suggest that the beneficial arginine residue at HCDR3 position 101 might interact with L chain residue tyr$^{49}$. To test this, L chain residue tyr$^{49}$ of clone CW43 was mutated to the lysine murine framework residue, resulting in a variant with a framework identical to clone 1H11 that also contained the beneficial arg$^{101}$ residue in HCDR3. The resulting mAb, termed Y49K, displayed 5-fold lower affinity than CW43. Thus, expression of tyrosine at L chain framework residue 49 or expression of arginine at HCDR3 residue 101 alone had no beneficial effect on the mAb affinity, while the concomitant expression of tyrosine and arginine at these sites improved the mAb affinity 5-fold. The non-additive, or dependent nature of the mutations demonstrates that L chain residue tyr$^{49}$ and HCDR3 residue arg$^{101}$ interact co-operatively to enhance the affinity of the mAb (Schreiber & Fersht, (1995)). In addition, the co-operative interaction that was observed between tyr$^{49}$ and arg$^{101}$ was also observed for variants that expressed lysine at HCDR3 position 101 (Table II).

Generally, interacting residues are spatially separated by no more than 7 Å (Schreiber & Fersht, 1995)). FIG. 3 shows molecular modeling of anti-CD40 variant CW43. A top view of the anti-CD40 variant CW43 variable region structure was created by homology modeling to examine the spatial relationship of L chain framework residue Y49 and H chain CDR3 residue R101. The L chain is on the left and the H chain right with the H chain CDR3 loop depicted in red. The L chain framework residue 49 is in close proximity to the H chain CDR3 loop and is 7 Å of the predicted interacting H chain CDR3 R101 residue. Although the interacting amino acids are located on distinct chains of the mAb, the residues are predicted to be within a range (7 Å) to permit co-operative interaction.

Throughout this application various publications have been referenced within parentheses. The disclosures of these publications in their entireties are hereby incorporated by reference in this application in order to more fully describe the state of the art to which this invention pertains.

Although the invention has been described with reference to the disclosed embodiments, those skilled in the art will readily appreciate that the specific experiments detailed are only illustrative of the invention. It should be understood that various modifications can be made without departing from the spirit of the invention. Accordingly, the invention is limited only by the following claims.

What is claimed is:

1. A method of identifying heteromeric variable region binding fragments comprising the steps of:
   a) providing:
      (i) a donor heteromeric variable region binding fragment comprising donor complementarity determining region reference sequences and a donor framework sequence wherein said donor variable region binding fragment binds an antigen and
      (ii) an acceptor framework sequence;
   b) comparing said donor framework sequence with said acceptor framework sequence;
   c) identifying one or more framework positions wherein said donor and said acceptor sequences are different;
   d) constructing a population of overlapping oligonucleotides said population of oligonucleotides encoding a population of overlapping fragments of a variable region of an antibody chain wherein said population of overlapping fragments comprise
      i) complementarity determining region sequences wherein at least one donor complementarity-determining region sequences is altered with respect to a donor complementarity-determining region reference sequence using codon based mutagenesis and ii) acceptor framework sequences modified by substitution with the donor amino acid more of said identified positions,
iii) said population of oligonucleotides comprising between 10 and $10^8$ different species;
e) extending the overlapping oligonucleotides to create a population of extended oligonucleotides encoding a population of acceptor variable regions;
f) generating a population of heteromeric variable region binding fragments comprising expressing said population of extended oligonucleotides to create a population of variable regions of antibody chains;
g) identifying individual heteromeric variable region binding fragments wherein said heteromeric variable region binding fragments bind the same antigen as said donor heteromeric variable region binding fragment.

2. The method of claim 1 wherein said complementarity-determining region sequences comprise at least one or more different amino acids in at least two complementarity-determining regions with respect to donor complementarity-determining region reference sequences.

3. The method of claim 2, wherein said complementarity-determining region sequences comprise at least one or more different amino acids in at least three complementarity-determining regions with respect to donor complementarity-determining region reference sequences.

4. The method of claim 1, wherein the population of extended oligonucleotides is expressed in a host cell selected from the group consisting of bacterial cells, yeast cells, insect cells and mammalian cells.

5. The method of claim 4, wherein said host cells are bacterial cells and said extended oligonucleotides are expressed in a bacteriophage expression system.

6. The method of claim 1 further comprising:
h) sequencing nucleic acid molecules encoding said identified heteromeric variable regions binding fragments;
i) identifying framework amino acids in said identified heteromeric variable region binding fragments that exhibit a biased representation at said selected framework positions with respect to said donor or said acceptor framework sequence.

* * * * *

```
                        SEQUENCE LISTING

<160> NUMBER OF SEQ ID NOS: 4

<210> SEQ ID NO 1
<211> LENGTH: 107
<212> TYPE: PRT
<213> ORGANISM: Mus musculus

<400> SEQUENCE: 1

Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser His Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Ile Tyr Tyr Cys Gln His Gly His Ser Phe Pro Arg
                85                  90                  95

Thr Phe Gly Gly Gly Thr Lys Leu Glu Ile Lys
            100                 105

<210> SEQ ID NO 2
<211> LENGTH: 107
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105
```

```
<210> SEQ ID NO 3
<211> LENGTH: 122
<212> TYPE: PRT
<213> ORGANISM: Mus musculus

<400> SEQUENCE: 3

Gln Ile Gln Leu Val Gln Ser Gly Pro Glu Leu Lys Lys Pro Gly Glu
 1               5                  10                  15

Thr Val Arg Ile Ser Cys Lys Ala Ser Gly Tyr Ala Phe Thr Thr Thr
            20                  25                  30

Gly Met Gln Trp Val Gln Glu Met Pro Gly Lys Gly Leu Lys Trp Ile
        35                  40                  45

Gly Trp Ile Asn Thr His Ser Gly Val Pro Lys Tyr Val Glu Asp Phe
    50                  55                  60

Lys Gly Arg Phe Ala Phe Ser Leu Glu Thr Ser Ala Asn Thr Ala Tyr
65                  70                  75                  80

Leu Gln Ile Ser Asn Leu Lys Asn Glu Asp Thr Ala Thr Tyr Phe Cys
                85                  90                  95

Val Arg Ser Gly Asn Gly Asn Tyr Asp Leu Ala Tyr Phe Ala Tyr Trp
            100                 105                 110

Gly Gln Gly Thr Leu Val Thr Val Ser Ala
        115                 120

<210> SEQ ID NO 4
<211> LENGTH: 113
<212> TYPE: PRT
<213> ORGANISM: Homo sapiens

<400> SEQUENCE: 4

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Tyr Phe Asp Tyr Trp Gly Gln Gly Thr Leu Val Thr Val Ser
            100                 105                 110

Ser
```